(12) United States Patent
Kapoor et al.

(10) Patent No.: US 8,175,892 B2
(45) Date of Patent: May 8, 2012

(54) SYSTEM AND METHOD FOR RADIATION THERAPY IMAGING AND TREATMENT WORKFLOW SCHEDULING AND OPTIMIZATION

(75) Inventors: Chetan Kapoor, Austin, TX (US); Edwin Jung, Austin, TX (US)

(73) Assignee: Agile Planet Inc., Austin, TX (US)

( * ) Notice: Subject to any disclaimer, the term of this patent is extended or adjusted under 35 U.S.C. 154(b) by 292 days.

(21) Appl. No.: 12/472,160

(22) Filed: May 26, 2009

(65) Prior Publication Data

US 2010/0303205 A1 Dec. 2, 2010

(51) Int. Cl.
*G06Q 50/00* (2006.01)
*A61N 5/00* (2006.01)

(52) U.S. Cl. ............... 705/2; 378/65; 705/7.27; 600/415
(58) Field of Classification Search .................. 705/2–3, 705/7.11–49; 378/20, 65, 68, 117, 195, 205, 378/209; 600/415
See application file for complete search history.

(56) References Cited

U.S. PATENT DOCUMENTS

| 4,578,757 | A  | * | 3/1986  | Stark ............................... 701/301 |
| 6,045,262 | A  | * | 4/2000  | Igeta et al. ..................... 378/209 |
| 6,651,279 | B1 | * | 11/2003 | Muthuvelan ........................ 5/600 |
| 7,268,358 | B2 | * | 9/2007  | Ma et al. ..................... 250/492.3 |
| 7,668,292 | B1 | * | 2/2010  | Bose et al. ....................... 378/65 |
| 7,746,978 | B2 | * | 6/2010  | Cheng et al. ..................... 378/65 |
| 2005/0234327 | A1 | * | 10/2005 | Saracen et al. ................. 600/407 |
| 2005/0281374 | A1 | * | 12/2005 | Cheng et al. ..................... 378/68 |
| 2008/0040151 | A1 | * | 2/2008  | Moore ............................... 705/2 |

* cited by examiner

*Primary Examiner* — Vivek D Koppikar
*Assistant Examiner* — Mark Holcomb
(74) *Attorney, Agent, or Firm* — The Jansson Firm; Pehr B. Jansson

(57) ABSTRACT

External beam radiotherapy treatment workflow scheduling and optimization. The system and method provides for determining a workflow metamodel, receiving a treatment plan, determining a treatment schedule corresponding to the workflow metamodel and treatment plan, taking into account safety by determining alternative treatment schedules, computing a safety index, and selecting one alternative treatment schedule that satisfies a safety threshold and that provides an optimal schedule.

60 Claims, 12 Drawing Sheets

SYSTEM AND METHOD FOR RADIATION THERAPY IMAGING AND TREATMENT WORKFLOW SCHEDULING AND OPTIMIZATION

BACKGROUND OF THE INVENTION

The present invention relates generally to radiotherapy systems, and more particularly to schedule optimization for delivery of external beam radiotherapy treatment.

Advances in technology have led to great progress in the treatment of many diseases. However, full utilization of the capabilities of the most powerful machines have not been fully realized because often the use of complex machinery must be carefully balanced against safety requirements. Adherence to safety requirements, which, of course, may not be compromised, often results in non-optimal use of machinery, unnecessarily long treatment sessions, and unnecessary expense both from non-optimized use of expensive equipment and from poor utilization of human resources.

The foregoing may be more true for radiation oncology than for any other medical field in that radiation oncology has been driven more by technological innovation involving complex, expensive and potentially hazardous equipment than most, if not all, other medical fields. External beam radiotherapy is a sophisticated treatment method for treatment of tumors and other medical conditions by aiming one or more collimated beams of energized ionizing particles to a desired location, a treatment volume, in a patient.

External beam radiotherapy is a form of treatment of, for example, cancers. A radiation source is used to produce a focused radiation beam, e.g., an x-ray beam that is aimed at a volume of interest in a patient. Typically, the volume of interest is a tumor. In many forms of radiation therapy, the treatment involves aiming a sequence of radiation beams from various angles towards the volume of interest. One reason for doing so is that by using beams from various angles may avoid delivering damaging radiation energy to healthy tissue in the path from the radiation beam delivery mechanism to the volume of interest and beyond. By having the multiple beams converge on the volume of interest a necrotic dose is delivered to the volume of interest while minimizing the damage to any healthy tissue that surrounds the volume of interest. This procedure involves many steps, which include positioning the radiation beams, re-configuring the cross-sectional profile of the beam and its intensity, and repositioning the patient and verifying correct positioning of the patient through re-imaging the patient. To allow for patient positioning, a patient is placed on a table that may be moved in six degrees of freedom, namely, x, y, and z-axis positions, and pitch, roll, and yaw rotations. Such a table may be robotically controlled.

Proton therapy is one particularly advanced form of external beam radiotherapy. Proton beams are produced for proton therapy by accelerating protons (hydrogen atoms without their electrons) in particle accelerators such as cyclotrons or synchrotrons. From the accelerator the protons are transmitted to a treatment room through a beam transport system. In the treatment room, the proton beam is focused through a nozzle placed very close to the patient.

An important advantage of proton therapy over, for example, photon radiation therapy, is that most of the energy of a proton beam is released at a specific location that may be accurately controlled. As protons enter the patient only a small amount of energy is released. However, the protons slow down as they pass through tissue and release a large amount of energy immediately before coming to rest. As a result, the energy associated with the protons may be delivered at a precise location with significantly less impact on surrounding tissue.

Manipulation of the lateral shape, through collimators, and energy of the beam using compensators, the proton beam may be given a three dimensional shape. Thus, the proton beam may be made to conform to the three-dimensional shape of a volume of interest. It must be appreciated that precise configuration of the proton therapy equipment and precise location of the patient, thereby precisely locating the volume of interest, is of critical importance. Consequently, a large portion of a treatment session is concerned with placement of the patient in the treatment room, modeling of the patient to allow for precise placement, and configuration of the equipment. Actual delivery of the treatment is usually a very small portion of the total treatment session.

Proton treatments are traditionally delivered using gantry systems, such as the system described in U.S. Pat. No. 7,348,579 to Eros Pedroni. In a gantry proton beam delivery system, a patient is positioned on a table and the proton delivery system is located on a rotating structure that may rotate around the patient to allow for delivery of the proton beam from many angles in the plane of rotation. In an alternative delivery mechanism the proton delivery system is fixed, for example, as fixed horizontal beam. In yet another alternative, the proton beam delivery system may incline between various angles to the vertical. In each of these systems, a patient positioning system is used to ensure that the patient, and, consequently, the volume of interest are positioned accurately so that the proton beam will deliver its energy to precisely the correct location.

In all forms of radiation therapy, accurate patient positioning is critical. In one form of proton therapy, known as Image-Guided Proton Therapy (IGPT), the patient positioning system is guided by a digital radiographic panel that may be moved in numerous ways around the patient positioning system to acquire x-ray images of the patient to verify accurate positioning of the patient and the volume of interest. The patient positioning systems may be further enhanced from additional imaging equipment such as optical tracking, ultrasound and electromagnetic signal emitting positioning systems.

Thus, treatment delivery may include many independent but linked steps involving patient simulation, patient positioning, equipment configuration and equipment movement. These steps may include several pieces of equipment that may move about the treatment room including the patient positioning system, the proton beam delivery system, and various forms of imaging equipment.

The delivery of radiation therapy is usually broken down into three stages: patient simulation, treatment planning, and treatment delivery. In patient simulation a patient is digitally modeled so that treatment planning and treatment delivery systems may have an accurate understanding of the shape and internal anatomy of the patient. Treatment planning includes designing a sequence of beams delivered from various directions relative to the patient and each beam having a particular shape and delivering a particular dose to the target. The main objective is to ensure that the beams in the treatment plan collectively deliver a destroying dose of radiation to the volume of interest while leaving surrounding tissue unharmed. U.S. Pat. No. 6,546,073 to Eva K. Lee, the entire disclosure of which is incorporated herein by reference, describes several treatment planning approaches including standard planning (or forward planning) in which a physician solves the problem of determining the appropriate dose distribution given a known set of beam characteristics and delivery parameters, and inverse treatment planning in which a computer optimization is performed from a set of parameters and dose distributions specified by physicians based on a set of pre-selected variables. Treatment delivery is the stage in which the treatment plan is executed to deliver the desired radiation treatment to a patient.

U.S. Pat. No. 6,546,073 further describes techniques for optimizing the treatment plan in terms of the selection of beams. However, while such optimization may produce more efficient and effective delivery of radiation to the tumor, the limitations of the equipment, the room setup, and delivery process are not considered. Furthermore, the order of beams in a plan may not be optimal with respect to treatment time or equipment motions. Hence there is still a need to optimize the actions of the actors involved in the delivery of a radiation treatment. Actors involved in the delivery of a radiation treatment include the radiation therapists (RTTs), the patient positioning system, multiple patient imaging devices, and the radiation delivery system. Because of the many independent actors involved, it is possible that a given workflow plan for delivery of a treatment plan involves steps that present danger to the patient or the equipment due to collisions between pieces of equipment or between equipment and patient. Because such situations are unacceptable, RTTs typically ensure safety by completely retracting equipment that may be retracted when other equipment is being positioned or when a patient is re-positioned. Such conservative measures are not efficient in terms of equipment use and time. A typical treatment session may take as long as one hour while the actual delivery of treatment is only 2-3 minutes of that time. Equipment placement, patient positioning, and patient imaging consume the remaining time of a treatment session.

Treatment planning fails to address duration of treatment sessions in terms of minimizing the time expended on inefficient workflow steps.

Interactive simulation of treatment rooms and radiotherapy equipment combined with accurate 3D patient specific data has been proposed, for example, in Hamza-Lup F. G, Sopin I, Lipsa D, and Zeidan O, (2007) X3D in Radiation Therapy Procedure Planning, International Conference on Web Information Systems and Technologies (WEBIST 2007), March 3-6, Barcelona, Spain (available at http://galati*armstrong*edu/research/webist07*pdf[1]), for improving treatment planning by using 3D equipment modeling and simulation to detect collisions among components used in delivering external beam radiation therapy treatments thereby saving time and resources in generating a treatment plan. This system, however, only provides for qualitative evaluation and visual inspection of different treatment configurations in a treatment plan. It is desirable to provide a quantitative evaluation of the quality of an entire treatment plan, rather than just individual configurations. Specifically, estimates of the treatment time, treatment safety, and treatment schedule are desired.

[1] Due to the prohibition of functioning hyperlinks in patents, all URLs herein are listed as www*xyz*com wherein each "*" is to be interpreted as a ".". Furthermore, this and other similar systems only model traditional couches and radiotherapy equipment used in photon therapy. Unlike existing patient positioning couches, robotic couches may execute arbitrarily complex trajectories in 3D space.

From the foregoing it will be apparent that there is still a need for an improved radiation therapy system and method of radiation therapy with improvement in duration of treatment sessions. Primary to such an improvement would be estimates for expected time required for execution of a workflow to deliver a treatment plan and evaluation of safety to patient and equipment expected during the delivery of a treatment according to a given workflow for delivery of a treatment plan.

DETAILED DESCRIPTION OF THE INVENTION

Figure 1A:
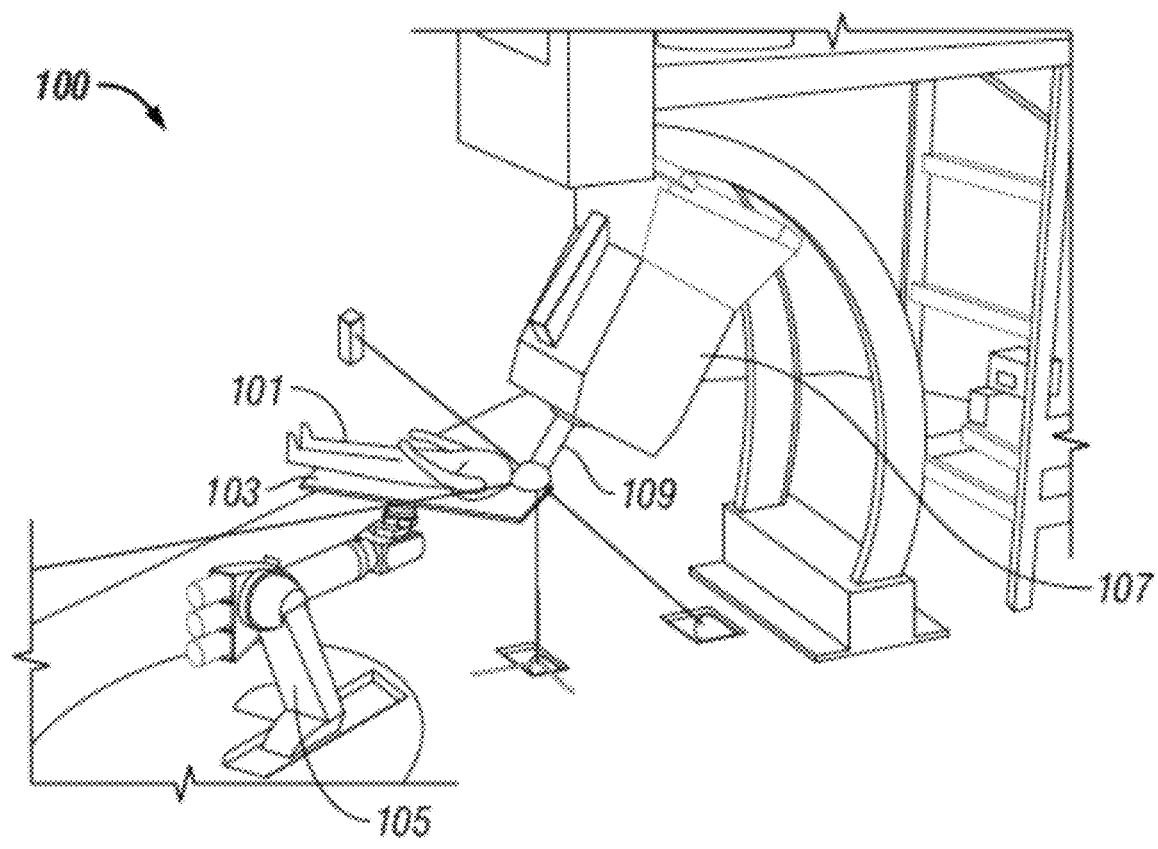
FIGS. 1(a) and 1(b) are perspective views illustrating, at a high-level, the pieces of equipment in a proton therapy treatment room.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein in connection with one embodiment may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

1.0 Introduction

An embodiment of a treatment planning scheduling and optimization system and method provides accurate estimates of the time and schedule expected to be expended when a workflow for delivery of a treatment plan is executed to deliver a radiation treatment. In an embodiment of a treatment plan scheduling and optimization system and method, a safety index is determined that confirms the viability of a proposed workflow for delivery of a treatment plan from a safety perspective. In an embodiment of the system and method for treatment plan schedule and optimization, alternative schedules are developed, examined for time expended and safety, thereby devising improved schedules when possible.

Figure 1B:
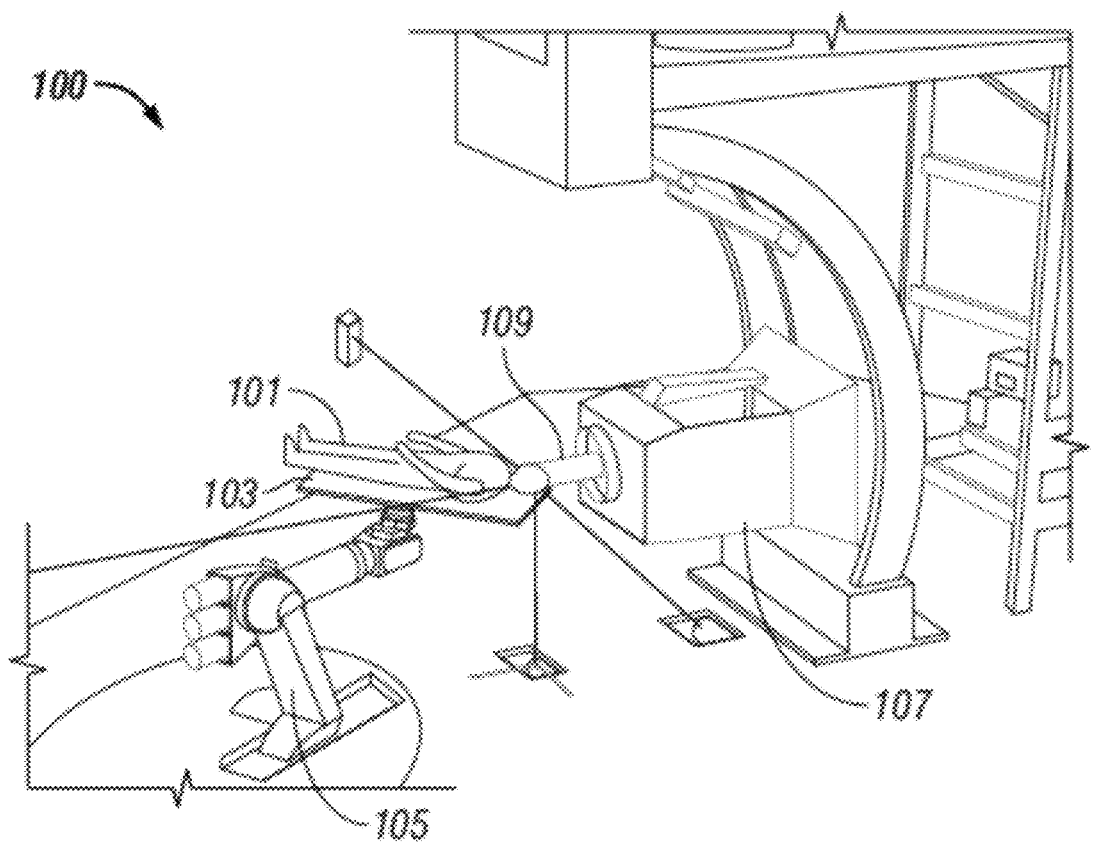

FIGS. 1(a) and 1(b) are perspective views illustrating, at a high-level, the pieces of equipment in a proton therapy treatment room 100. A patient 101 is lying down on a couch 103 of a patient positioning system 105. An inclined beam proton delivery system 107 capable of delivering beams either in a horizontal position (as illustrated in FIG. 1(b)) or in an inclined position, e.g., 30 degrees off the vertical (illustrated in FIG. 1(a)). The proton delivery system 107 includes a nozzle 109. The nozzle 109 includes an extendable component referred to as a snout that may include a collimator and a compensator for focusing the proton beam and giving the proton beam a contour that conforms to the shape of a targeted volume of interest. During a treatment session, it is often necessary, as part of a treatment plan, to change or reconfigure the snout, e.g., moving it in or out of the nozzle 109 or making changes to the collimator and compensator when going from one field to the next in delivering a sequence of fields (a field is delivery of treatment from one beam of radiation at a particular configuration).

A critical aspect of radiation therapy is accurate and precise placement of the patient 101 with respect to the radiation delivery system 107. The patient positioning system 105 may position the patient in six degrees of freedom: translation along the x, y, and z axis, roll, pitch and yaw. To orient the patient with respect to the radiation delivery system 107, all equipment and the patient 101 is modeled with respect to the treatment room coordinate system.

Figure 2:
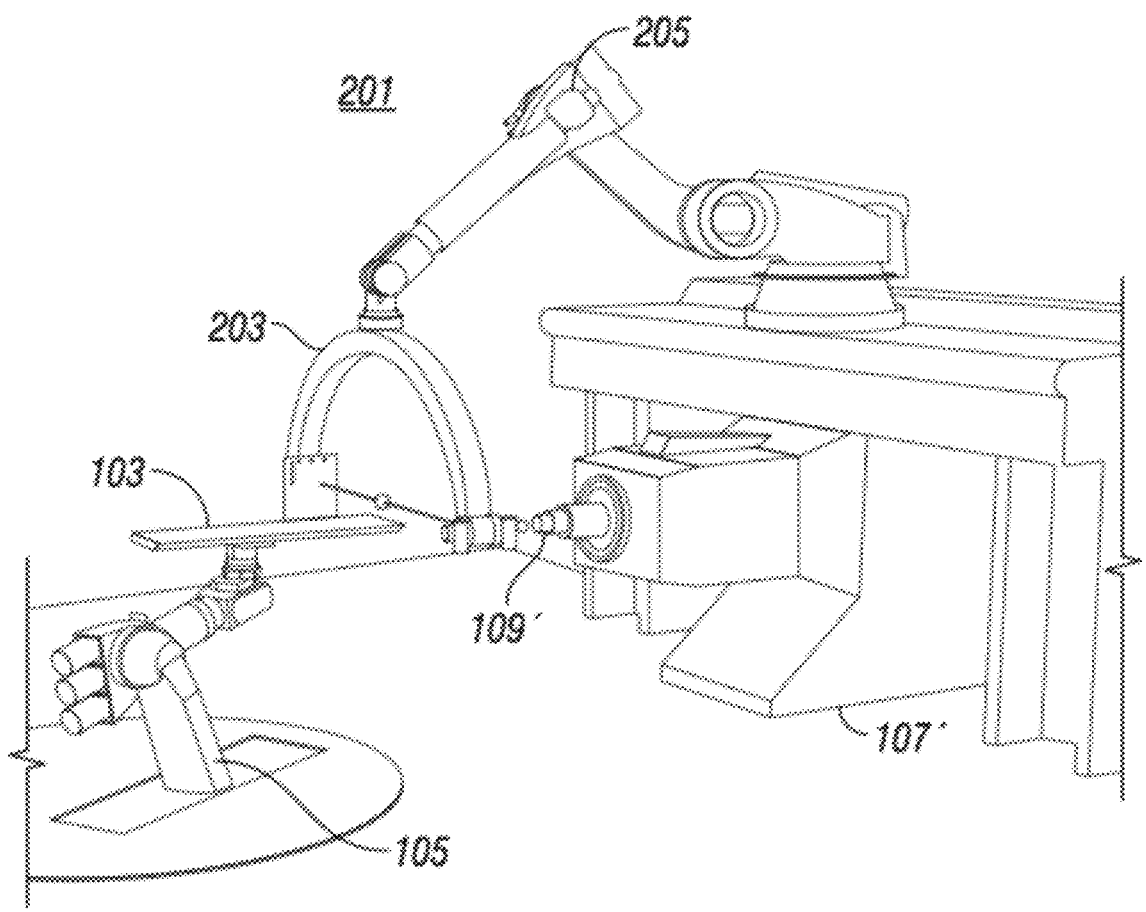
FIG. 2 is a perspective view of a one type of imaging system that may be used to image a patient in conjunction with a fixed horizontal beam proton treatment system.

Accurate patient positioning requires modeling of the patient 101. This occurs, at least twice, prior to treatment and during the treatment session itself. To enable accurate placement of the patient 101, the patient 101 is imaged using various imaging systems such as CT scanner and MRI. FIG. 2 is a perspective view of a one type of imaging system 201 that may be used to image a patient 101 in conjunction with a fixed horizontal beam proton treatment system 107. The imaging system 201 is a robotic device having a C-arm 203 that may be moved around the patient 101 to permit imaging the patient 101 using a robot 205 to allow imaging the patient 101 from a large range of angles and from many different vantage points along the length of the patient 101.

2.0 Radiotherapy Treatment Room Equipment

Figure 3:
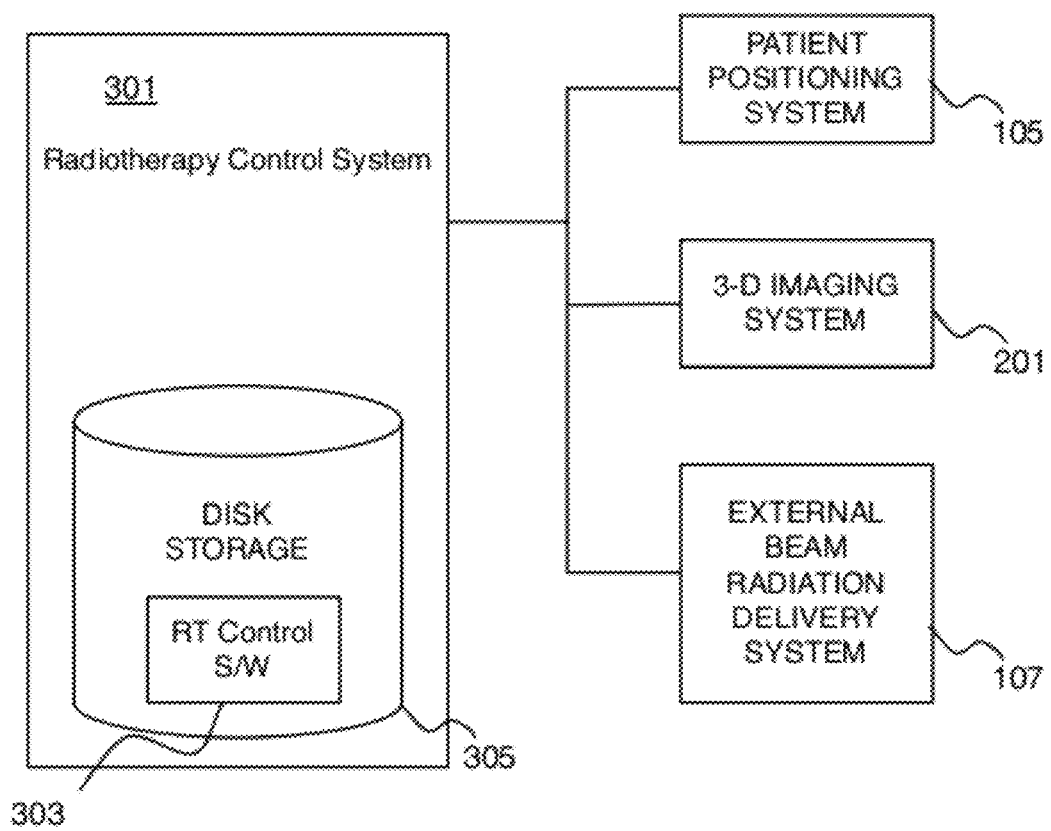
FIG. 3 is a high-level schematic diagram illustrating the radiotherapy control system connections to the patient positioning system, the imaging system, and external beam radiation delivery system of FIGS. 1 and 2.

The equipment used in a treatment room is typically controlled from a radiotherapy control system that may be used to control the movement and operation of the pieces of equipment, e.g., the imaging systems and patient positioning systems, as well as, the proton beam delivery system 107. In one embodiment, the patient positioning system 105, the 3D imaging system 201, and external beam radiation delivery system 107 are robotic equipment that perform their respective actions in response to control signals transmitted from the radiotherapy control system 301. FIG. 3 is a high-level schematic diagram illustrating the radiotherapy control system 301 connections to the patient positioning system 105, the 3D imaging system 201, and external beam radiation delivery system 107. The radiotherapy control system 301 is, in turn, controlled by radiotherapy software 303 (discussed herein below) stored on a disk storage device 305.

3.0 Treatment Planning and Treatment Delivery

Figure 4:
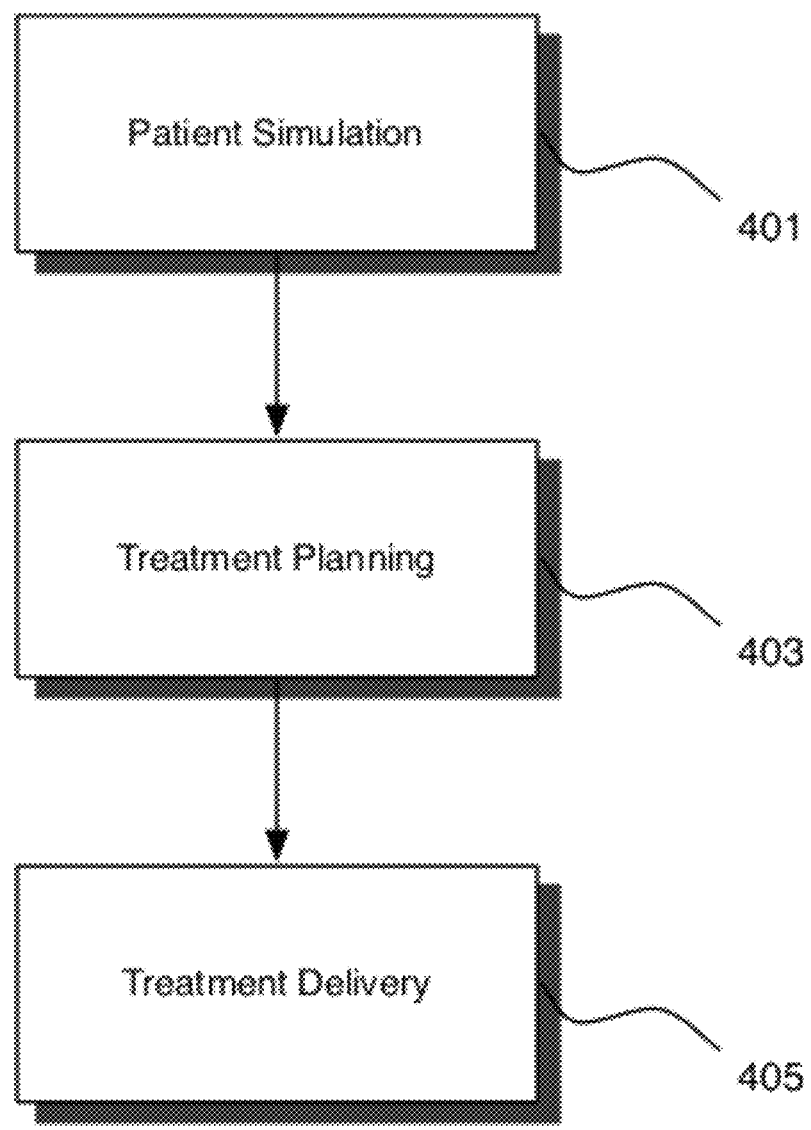
FIG. 4 is a high-level flow diagram illustrating the prior art treatment planning and delivery workflow.

Traditionally treatment planning and delivery consists of three distinct stages as illustrated in FIG. 4, which is a high-level flow diagram illustrating the prior art treatment planning and delivery workflow. The first step, a preliminary step, is patient simulation 401. In patient simulation, the patient 101 is scanned using one or more imaging systems such as CT scanning, PET scanning, and MRI scanning. These images are used to create a three-dimensional model of the patient 101 including the volume of interest for treatment. The 3D model of the patient 101 and volume of interest is later used to specify the treatment plan and to accurately position the patient 101 with respect to the treatment equipment during treatment delivery. The patient simulation step 401 may include identifying and marking immovable structures, e.g., bones, which may later be used to position the patient 101 and the relationship between those structures and volumes of interest.

Next a dosimetrist or a radiation oncologist uses a treatment planning system (TPS) to identify volumes of interest, i.e., tumors to be treated and sensitive areas for which unnecessary radiation should be avoided or minimized in the model, step 403. The treatment planning 403 results in a specification of a set of treatment fields. Each treatment field specifies radiation beam properties (in the case of proton therapy, proton beam properties) including range, aperture, intensity and direction. The treatment plan 403 also includes position and orientation of the patient 101 with respect to the treatment room isocenter, i.e., the location in the treatment room through which the center of the radiation beams pass. The treatment plan 403 also specifies geometric properties of the collimator and the compensator defining the properties of the treatment fields.

The treatment planning stage 403 may be followed by a verification step in which a RTT manually verifies and adjusts the treatment plan to identify potential safety hazards and to reduce the overall duration of a treatment session.

Finally, once the treatment plan 403 has been finalized, a treatment delivery stage 405 begins. During the treatment delivery stage 405, one or more beams of radiation, e.g., proton beams, are delivered to the patient 101. For each beam, the patient positioning system 105 and, consequently, the patient 101 are moved into the desired position and orientation to place the volume of interest to be treated in the correct position and orientation under the beam delivery system 107. Further, the beam nozzle 109 may be moved to a specified angle.

Treatment delivery 405 may further include reconfiguration of the beam by selecting specific compensator, collimator (thereby changing the aperture of the beam), and extension of the beam nozzle 109. These items define the extent of penetration depth of the cross-section of the beam, the shape of the cross-section of the beam, and the proximity of the beam to the skin of the patient 101, respectively.

Treatment delivery 405 involves the sub-steps of patient positioning and treatment field delivery. During patient positioning, the patient 101 is positioned using the patient positioning system 105 such that the volume of interest is located at the treatment room isocenter. The RTT uses the imaging system 201 to acquire x-ray images of the patient's area of interest. These images are used to register the specific volume of interest position accurately in the treatment room coordinates. When the patient has been positioned and registered to verify accurate positioning, a treatment field is delivered. The process of beam configuration, patient positioning and registering (if necessary after a patient repositioning or to confirm that the patient has not moved), and field delivery is repeated for all fields in the treatment plan.

4.0 Improved Treatment Planning

Figure 5:
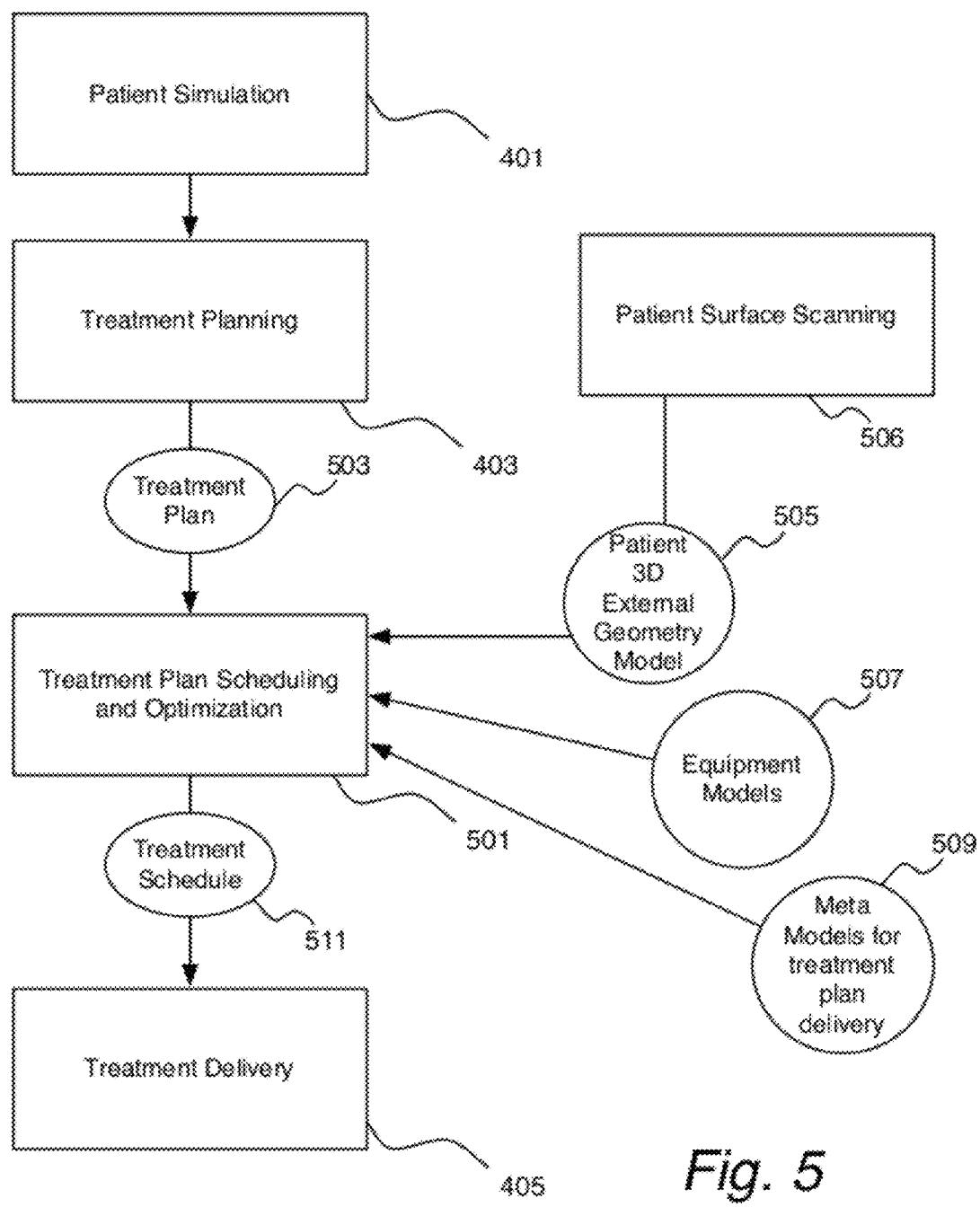
FIG. 5 is a high-level flow diagram illustrating an improved radiotherapy workflow in which the treatment plan produced by the treatment planning stage is input to a treatment planning scheduling and optimization stage which produces a model of the treatment schedule with safety indexes and timing information which may be used by a radiotherapy technician, dosimetrist, or treatment planner, or treatment planning software to verify or revise the treatment plan.

In an improved radiotherapy workflow illustrated in FIG. 5, which is a high-level flow diagram illustrating an improved radiotherapy workflow according to the invention, the treatment plan 503 produced by the treatment planning stage 403 is input to a treatment planning scheduling and optimization stage 501 which produces a treatment schedule 511 with safety indexes, and timing information which may be used by a dosimetrist, a treatment planner, e.g., a radio therapy physician, or a radio therapy technician, or even treatment planning software, to verify or revise the treatment plan.

Figure 8:
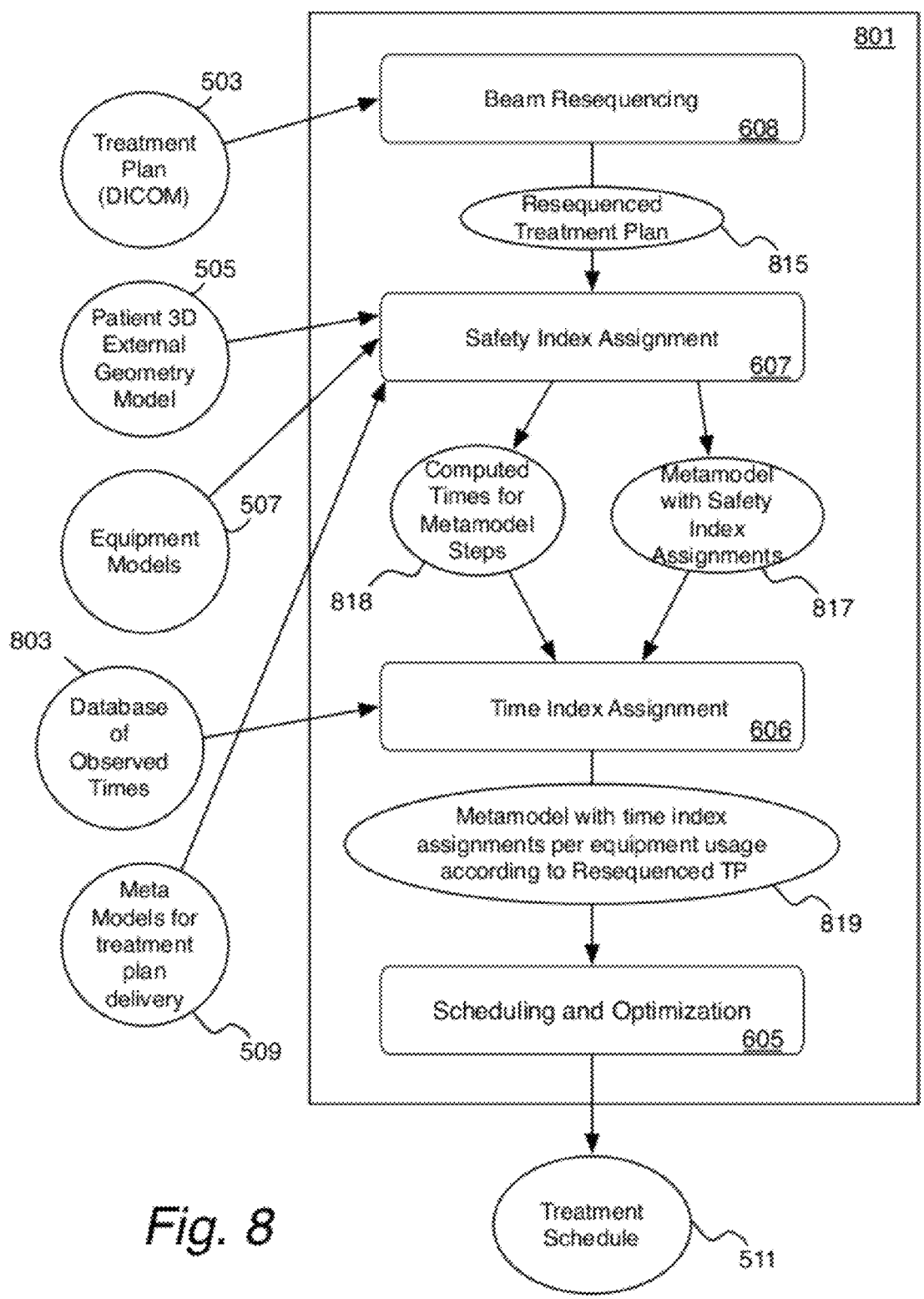
FIG. 8 is a flow-chart illustrating the process for generating schedules generated from the metamodel as illustrated in and described in conjunction with FIG. 6.
Figure 9:
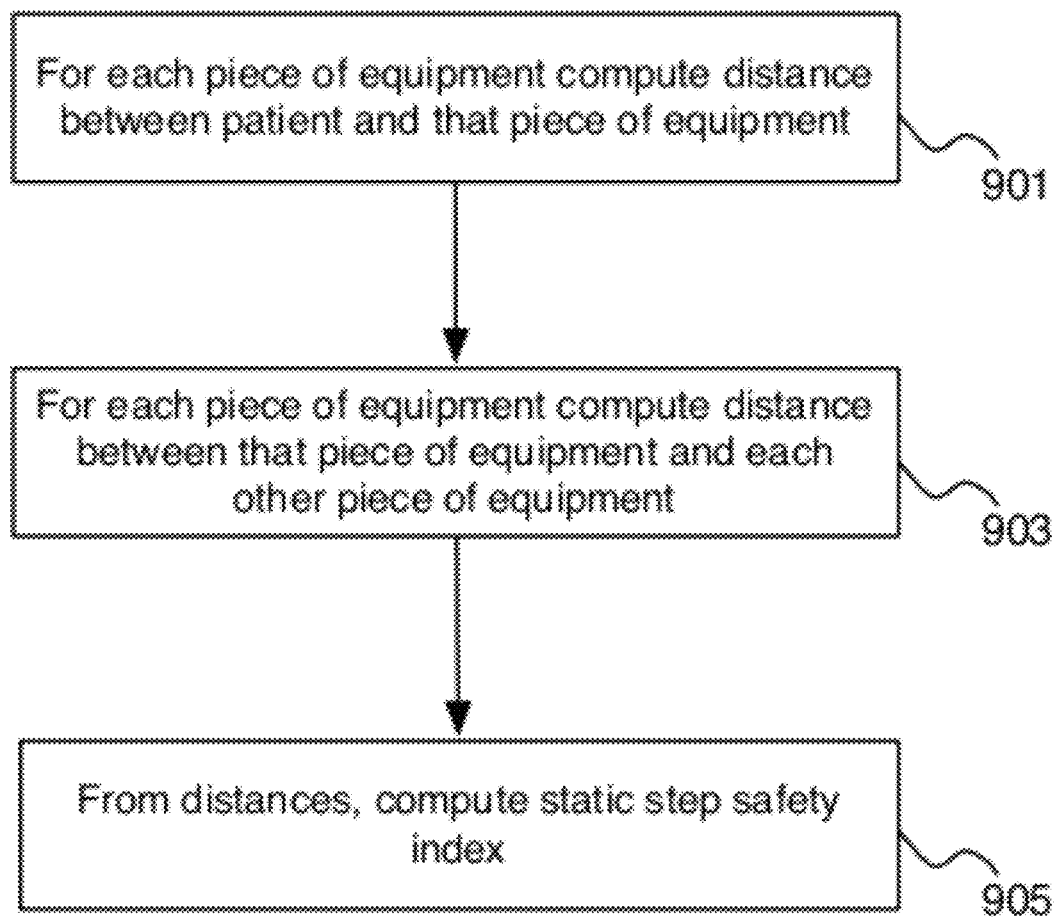
FIG. 9 is a flow-diagram illustrating the computation of a collision safety index based on workflow steps.
Figure 10:
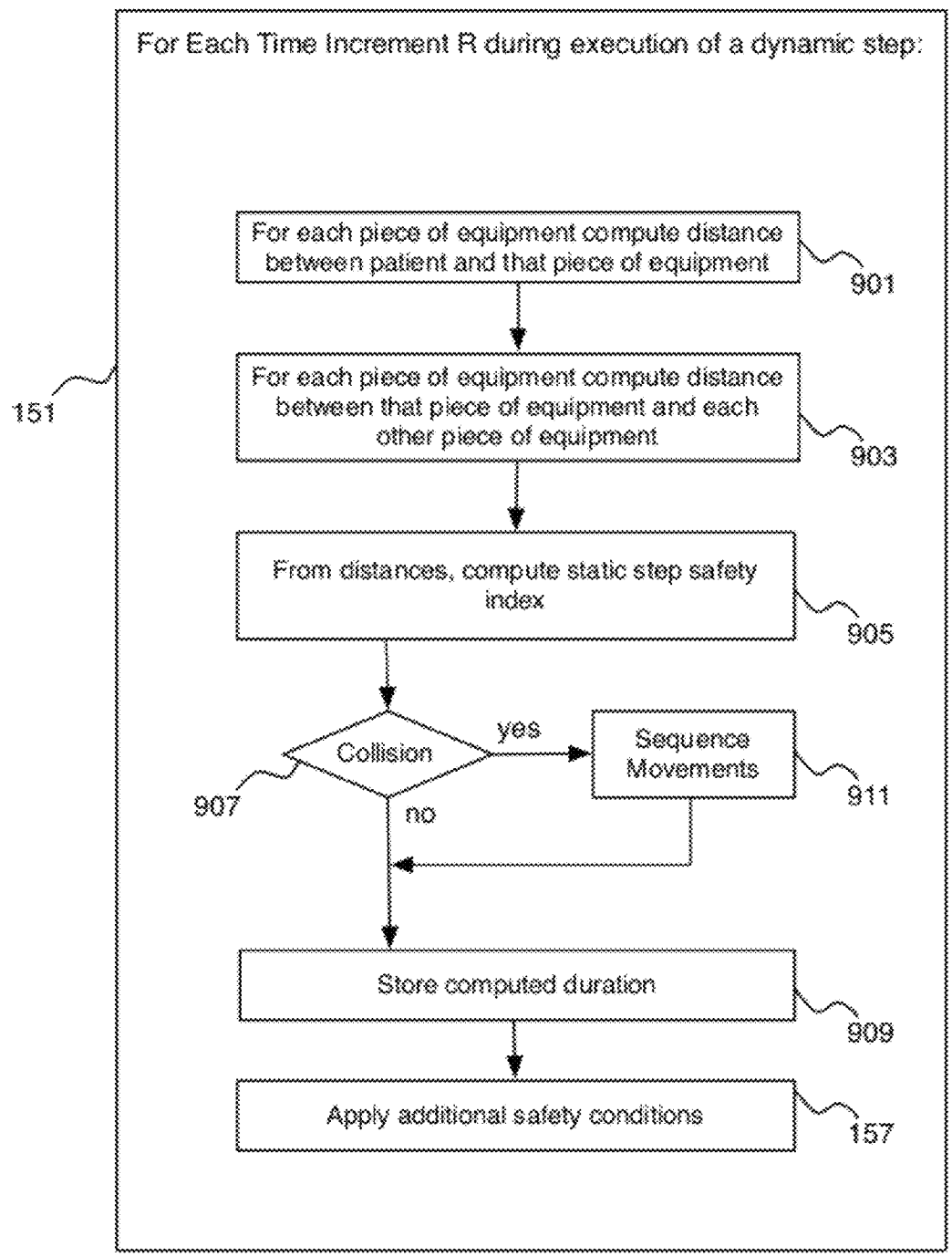
FIG. 10 is a flow-diagram illustrating the computation of a safety index based on dynamic workflow steps, i.e., workflow steps with at least one piece of equipment in motion.

A method for carrying out the treatment planning and optimization stage 501 is illustrated in and described in conjunction with flow-charts of FIGS. 8, 9, and 10.

One input to the treatment plan scheduling and optimization stage 501 is a treatment plan 503. A treatment plan 503 consists of multiple beam configurations. Each beam configuration involves the patient 101, the patient positioning system 105, the radiation delivery system 107, and the nozzle 109 attachments (e.g., collimator and compensator). Each unique configuration in a treatment plan 503 may require the patient positioning system 105 to be moved, the angle of the radiation delivery system 107 to be changed, or the collimator and compensator that are attached to the beam nozzle 109 be switched to another collimator or compensator, respectively. In a preferred embodiment the treatment plan 503 is a DICOM treatment plan.

Actual delivery of a treatment plan requires a treatment schedule which specifies the sequence and timing of activities that should occur to deliver treatment according to a particular treatment plan. The treatment schedule consists of multiple activities involving a RTT, the patient 101, the patient positioning system 105, the radiation delivery system 107, the nozzle 109 attachments (e.g., collimator and compensator), and imaging systems 201. According to a treatment schedule, for any given step of that schedule, the patient positioning system 105 and the radiation delivery system 107 may be moved to new positions or placed in new configurations, either automatically or manually with intervention from an RTT.

The treatment plan scheduling and optimization stage 501 accepts as input a metamodel 509 of the treatment workflow. An example of such a metamodel 509' is illustrated and metamodels 509 are described in greater detail in conjunction with FIG. 6. A metamodel 509 is a set of rules and constraints for delivering the treatment plan 503. A metamodel 509 represents the treatment workflow as a set of steps, wherein each step establishes precedence relationships to other steps in the treatment workflow. The steps also list the required resources and actors (e.g., RTT, the patient positioning system 105, radiation delivery system 107, the patient 101) and attributes (e.g., duration, cost, safety). The metamodels 509 are developed by observing the delivery of treatments in a radiotherapy treatment room.

The treatment planning scheduling and optimization stage 501 also accepts as input a three dimensional patient surface-scanning model 505 which is produced using patient surface scanning equipment and modeling tools 506, e.g., CT scanning equipment and software capable of building 3D models of the patient from CT scans, camera based systems (e.g., Vison RT, www*visionrt*com), laser scanning (e.g., LAP Laser, www*lap-laser*com).

Further inputs to the Treatment Plan Scheduling and Optimization stage 501 are equipment models 507 for the various pieces of equipment used in delivering radiotherapy treatments, including the treatment room itself, the patient positioning system 105, the imaging equipment 201, and the external beam delivery system 107. There are several different approaches to equipment modeling, e.g., workcell modeling which may be described as geometric modeling of a workcell, which models the position, size, and shape of all objects in a workcell, e.g., a treatment room, and the relational speed and acceleration among them. Workcell modeling is described in detail in Knoll, J. A., May 2007, *Complete Workcell Modeling for Robot Control and Coordination*, Master's Thesis, University of Texas at Austin, 180 p., the disclosure of which is incorporated herein by reference in its entirety.

Using the patient surface model 503, 3D geometric equipment models 507 for the radio-therapy equipment and the treatment room, and metamodels 509 for operations carried out to deliver a treatment plan, the treatment plan scheduling and optimization stage 501 produces a treatment schedule 511 with an estimated overall quality with respect to time or safety. The time and safety estimates may also be used to identify bottlenecks in the treatment schedule 511 and to suggest modifications to the treatment plan 503 thereby leading to an optimized treatment schedule that conforms to specified safety requirements.

Figure 6:
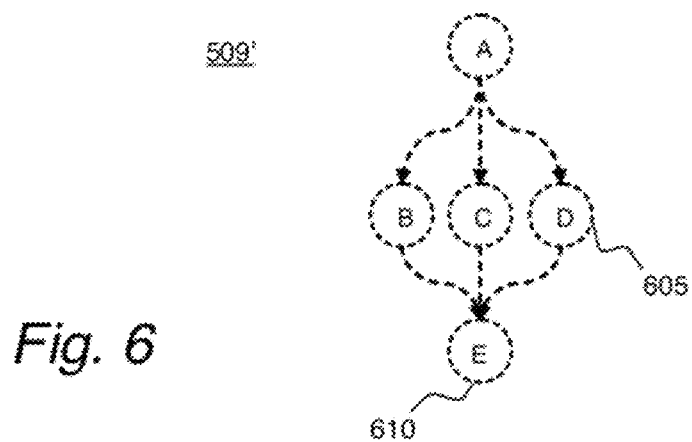
FIG. 6 is a schematic illustration of an exemplary workflow metamodel describing the delivery of a treatment plan.
Figure 7:
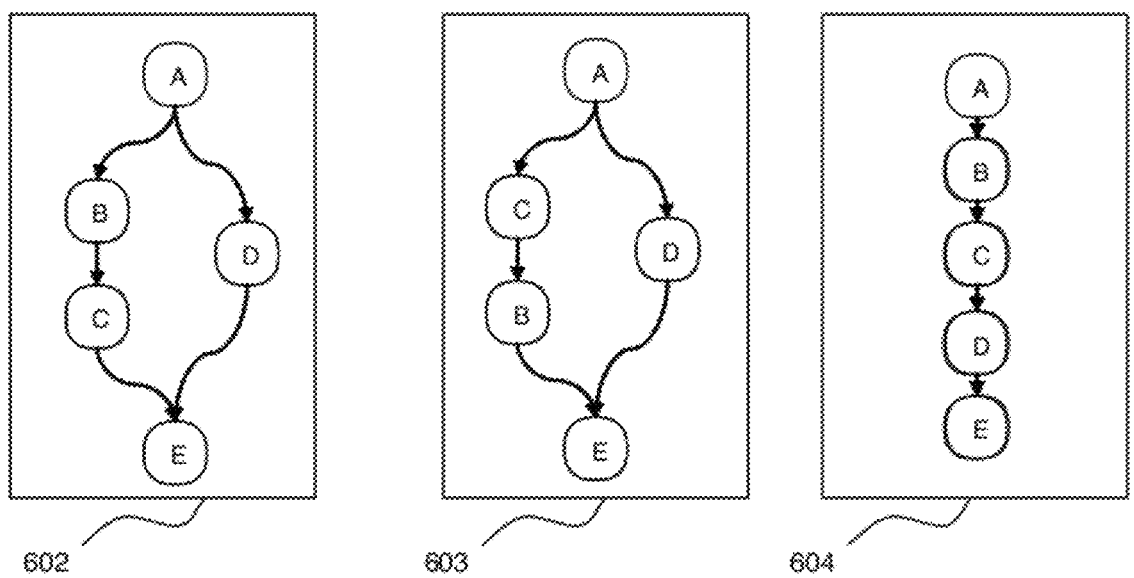
FIG. 7 is a schematic illustration showing different schedules generated from the workflow metamodel of FIG. 6.

Turning now to a description of workflow metamodels 509, FIG. 6 contains a schematic illustration of an exemplary workflow metamodel 509' describing the delivery of a treatment plan. FIG. 7 is an illustration of several possible schedules 602, 603, and 604 for delivering the treatment plan corresponding to the workflow metamodel 509'.

Each node in a workflow metamodel 509, e.g., nodes A, B, C, D, and E in the exemplary workflow metamodel 509', represents a distinct step in the workflow for delivery of a treatment plan 503. For the example, the information attached to each node in the exemplary workflow metamodel 509' is listed in Table I below.

TABLE I

Example workflow metamodel

| Node | Action | Actors/Resources | Relations | Duration |
|---|---|---|---|---|
| A | Place Patient in Fixation Device | Couch & RTT | None | 120 s |
| B | Take X Axis Image | Couch & X-Ray | A > B | 30 s |
| C | Take Y Axis Image | Couch & X-Ray | A > C | 30 s |
| D | Change Compensator | Beam & RTT | A > D | 240 s |
| E | Move Patient to Isocenter | Couch | B > E, C > E, D > E | 160 s |

For example, node E 610 requires that the patient positioning system ("couch") 105 be moved to a location for beam delivery. Each node in the workflow defines the actors and resources involved, for example, for Node D 605 both the radiotherapy delivery equipment 107 and a RTT are required. Similarly, the patient positioning system 105 ("couch") is involved in Step E 610. The workflow metamodel 509 defines a precedence relationship between the steps, e.g., in the case of the example of workflow metamodel 509', step E is executed after steps B, C, and D.

Each node is annotated with the expected amount of time required to execute that step and the actors involved in the step. Thus, for example, step E 610 is estimated to take 160 seconds to execute. The information on expected duration of particular steps are either determined by observation of treatment delivery, or by executing models describing acceleration and velocity of equipment involved in performing the operations as described in Section 5.0.

Activities that occur on separate branches are independent, and may occur in parallel, if no constraints are violated. For example, the metamodel 509' shows that the steps "Take X Axis Image" (Node B), "Take Y Axis Image" (Node C), and "Change Compensator" (Node D) may occur in any order since they are on separate branches. However, because Nodes B and C both require "Couch & X-Ray," either Node B must occur first or Node C must occur first.

The sample metamodel 509' of FIG. 6 represents a series of logical statements and properties regarding each step, and the relationships between steps. These are summarized in Table II:

TABLE II

| Symbol | Logical Statement or Property |
|---|---|
| Node | Action |
| Edge between nodes A and B | One or more of the following: $end_A < start_B$ (The step represented by A must end before B starts.) $end_A = start_B$ (The step represented by B must start when A ends) |
| Duration of Node A | The activity represented by A will require the specified time to complete. |
| Actors and Resources of Node A | The activity represented by A will require the set of actors and resources specified by the node. |

A schedule, which includes an estimate of the time to completion, requires the assignment of specific resources and starting and ending times for each step. These assignments may be made manually or automatically by a scheduling algorithm, as described herein below. The example metamodel 509' has three associated feasible schedules 602, 603, and 604 illustrated in FIG. 7.

5.0 Treatment Plan Scheduling and Optimization Process 801

FIG. 8 is a flow-chart illustrating the steps of a process 801 for providing the treatment plan scheduling and optimization step 501 of an improved radio-therapy workflow which produces a treatment schedule 511 having safety indexes, and timing information.

The process 801 accepts as inputs a treatment plan 503 from the treatment planning stage 403, a patient 3D external geometry model 505 from the patient surface scanning equipment and modeling software 506, the equipment models 507, the relevant metamodels 509 that model treatment plan delivery, and a database 803 having observed execution times for certain metamodel 509 steps.

5.1 Beam Resequencing

A first step of the process 801, is beam resequencing, step 608.

A treatment plan 503 presents a fixed number of fields to be delivered. These fields may be reordered. Currently, radiotherapists perform this reordering manually before treatment delivery, based on past experience with the equipment. In an embodiment of the invention, the beams of the treatment plan 503 may be resequenced in a beam resequencing stage 608.

The sequence of these beams may be arbitrarily rearranged as desired by the RTT before treatment delivery. This ordering of the beam sequence impacts the overall execution time and complexity of the treatment delivery. Traditionally, an RTT manually arranges beam sequence that expedites the treatment process relying on the particular RTT's past experience in treatment delivery.

According to one embodiment, the Treatment Scheduling and Optimization Module 501 automates the process of beam sequencing before generating a schedule for the treatment plan. The general principle behind the automatic beam sequencing is that the sequence should minimize magnitude of configuration changes and patient movements between beams.

Each beam contains the following information:
1. Snout Selection
2. Compensator Thickness
3. Gantry Angle
4. Patient Support Angle
5. Isocenter Position (x, y, z)
6. Snout Extension
7. Field ID The beam sequence is automatically determined by sorting according to the factors that most affect the execution time. The sorting rules include:

1. Beams are first partitioned into sets by snout selection. Snout changes require manual intervention and parking of all pieces of equipment. Hence snout changes often consume more time than other treatment delivery steps.
2. For each set of snouts, the beams are partitioned into sets by compensator thickness. Compensator changes also require manual intervention and parking of all pieces of equipment, and consume significant time.
3. For each set of compensator thicknesses, the beams are sorted by beam delivery angle. Changes to the beam delivery angle require movement of both the patient positioning system and the beam delivery system 107.
4. For each beam delivery angle, the beams are sorted by the angle of the patient positioning system 103. Changes to patient support angle only require movements by the patient positioning system 103.
5. For each set of patient support angles, the beams are sorted by isocenter position. Changes to isocenter position only require movements by the patient positioning system 103.
6. Finally, for each set of isocenter positions, beams are sorted by snout position. Snout position changes only involve small movements of the snout 109.
7. Field ID is simply a unique name for each beam and is ignored.

A mathematical ordering relation can be used to describe the above process. Generally, it is desirable to minimize the magnitude of the configuration changes between beams. If an ordering relation can be defined on the set of all beams, then minimizing the magnitude of configuration changes can be accomplished simply by sorting the beams.

More formally, the beam sequence is automatically determined by defining a lexicographical partial order relation on the Cartesian Product of beam elements. A beam is defined as:

$$Beam = (s, c, g, p, i, e, f)$$

where $s \in S$, $c \in R$, $g \in R$, $i \in R^3$, $e \in R$, $f \in R$. S is the set of snout names, R is the set of real numbers and $R^3$ is the set of real triples.

In other words, a beam is defined as a snout selection, compensator thickness, beam delivery angle (or for gantry systems, gantry angle), patient support angle, isocenter, snout extension, and field id. The set of all beams is defined by the product of all possible configuration variables. A treatment plan is a set of beams, and the beam resequencing step 608 sorts these beams first by s, then by c, g, p, i, e, and f, respectively.

Lexicographical ordering is also used to sort words in the dictionary, where each element (i.e., letter) in a word is compared sequentially to determine the order. By analogy, a beam (word) is composed of elements, and each element is compared sequentially to determine the order.

The particular definition of the beam above (s, c, g, p, i, e, f) is chosen to minimize the number of configuration changes that must occur to deliver a treatment plan. The introduction of new treatment equipment or changes to the treatment process may require a different definition of beam elements.

For example, if the treatment process were changed such that an x-ray was required after every change of isocenter position, the cost of an isocenter change would become greater than changing the beam delivery angle or patient support angle. Then the desired definition of beam elements would be (s, c, i, g, p, e, f).

In general, the definition of the beam is chosen such that the highest cost elements come before the other elements.

For example, a beam sequence as exported from the treatment planning system is displayed in the Table III, entitled 'Original Beam Sequence' below. After sorting, the optimized beam sequence, as described above, is shown in the Table IV, entitled 'Optimized Beam Sequence.' The beam definition used is (s, c, g, p, i, e, f).

TABLE III

Example Original Beam Sequence
Original Beam Sequence

| Field ID | Snout Selection | Compensator Thickness | Gantry Angle | Patient Support Angle | Isocenter Position | Snout Extension |
|---|---|---|---|---|---|---|
| 1 | 12 cmdiam | 58.53 | 90 | 0 | 31.46, −7.74, −106.5 | 189.9 |
| 2 | 12 cmdiam | 68.15 | 90 | 40 | 31.46, −7.74, −106.5 | 194.8 |
| 3 | 12 cmdiam | 101.87 | 90 | 137 | 31.46, −7.74, −106.5 | 246 |
| 4 | 15 cmdiam | 77.31 | 30 | 0 | 31.46, −7.74, −106.5 | 212.1 |
| 5 | 12 cmdiam | 53.21 | 90 | 0 | 31.46, −7.74, −106.5 | 109.9 |
| 6 | 12 cmdiam | 65.24 | 90 | 60 | 31.46, −7.74, −106.5 | 151.2 |
| 7 | 15 cmdiam | 86.32 | 90 | 125 | 31.46, −7.74, −106.5 | 184.2 |
| 8 | 15 cmdiam | 78.58 | 30 | 0 | 31.46, −7.74, −106.5 | 162.1 |

TABLE IV

Example Optimized Beam Sequence
Optimized Beam Sequence

| Field ID | Snout Selection | Compensator Thickness | Gantry Angle | Patient Support Angle | Isocenter Position | Snout Extension |
|---|---|---|---|---|---|---|
| 5 | 12 cmdiam | 53.21 | 90 | 0 | 31.46, −7.74, −106.5 | 109.9 |
| 1 | 12 cmdiam | 58.53 | 90 | 0 | 31.46, −7.74, −106.5 | 189.9 |
| 6 | 12 cmdiam | 65.24 | 90 | 60 | 31.46, −7.74, −106.5 | 151.2 |
| 2 | 12 cmdiam | 68.15 | 90 | 40 | 31.46, −7.74, −106.5 | 194.8 |
| 3 | 12 cmdiam | 101.87 | 90 | 137 | 31.46, −7.74, −106.5 | 246 |
| 4 | 15 cmdiam | 77.31 | 30 | 0 | 31.46, −7.74, −106.5 | 212.1 |
| 8 | 15 cmdiam | 78.58 | 30 | 0 | 31.46, −7.74, −106.5 | 162.1 |
| 7 | 15 cmdiam | 86.32 | 90 | 125 | 31.46, −7.74, −106.5 | 184.2 |

The output of the beam resequencing step 608 is a resequenced treatment plan 815.

5.2 Safety Index Assignment

A next step of process 801, is safety index assignment, step 607. The safety index may range in value between 0 (implying a safety violation) and 1 (signifying a high confidence in the safety of an operation). The safety index calculation of the workflow-step is based on a Collision Safety Index and a Dynamic Safety Index.

The Safety Index Assignment step 607 accepts as inputs the resequenced treatment plan 815, the patient 3D external geometry model 505, equipment models 507 and the metamodel 509 for treatment plan delivery.

5.2.1 Collision Safety Index

Collision safety can be evaluated by determining the minimum possible distance that any pair of items could approach during the treatment delivery.

Collision modeling may accept as input the locations and orientations of each object in the treatment room, including the patient 101, a configuration file which provides the relationship between objects in the room, and object geometries for each object in the treatment room. The object models include patient surface scanning models describing the geometric shape of the patient 101.

A homogenous transformation matrix is used to specify the location and orientation of each object in the treatment room. These matrices are 4×4 matrices wherein the upper left 3×3 part represents the orientation of the object with respect to a base coordinate frame. The top three entries of the last column of the homogenous transformation matrix represent the position of the object with respect to the base coordinate frame. This matrix T is represented in Table V below:

TABLE V

Transformation Matrix describing position and orientation of an object

| $n_x$ | $o_x$ | $a_x$ | $p_x$ |
|---|---|---|---|
| $n_y$ | $o_y$ | $a_y$ | $p_y$ |
| $n_z$ | $o_z$ | $a_z$ | $p_z$ |
| 0 | 0 | 0 | 1 |

A given object in the treatment room that does not change position has associated therewith a predefined static transformation matrix. For a non-stationary object, the associated transformation matrix is a function of the kinematic structure of the object, and its actuated components. For example, an object that moves along a straight line along the X coordinate system has a transformation matrix whose $p_x$ value changes as a function of the position of the object along the X axis. An object, such as the nozzle (figure reference) that moves along a circular path will have its transformation matrix change as a function of angle of the beam delivery system 107.

The position of each rigid link of the patient positioning system 105 is computed using the same principles as described above. However, as the patient positioning system 105 comprises of multiple rigid bodies that are connected by robotic joints, the transformations associated with a given link are dependent on the transformation associated with the links preceding it in the kinematic chain. The relationship between any two adjacent links of the patient positioning system 105 is represented by a homogenous transformation matrix such as the one shown above. The values of this transformation matrix change based on the position of the robotic joint. The Cartesian position of a given link of the robot is then computed by multiplying the individual transformation matrices of each joint of the robot that precede the link in question. For example, a transformation that represents the Cartesian position and orientation of link 4 of the robot will be computed as such:

$T_{b4}=T_{b1}*T_{12}*T_{23}*T_{34}$, where $T_{b4}$ is the transformation between the base coordinate system and the 4$^{th}$ link of the robot, $T_{b1}$ is the transformation between link 1 of the robot and the base coordinate system, $T_{12}$ is transformation between link 1 and link 2 of the robot, $T_{23}$ is the transformation between link 2 and 3 of the robot, etc.

By generalizing the method above, the Cartesian position and orientation of each rigid body can be computed based on the type of input that moves that rigid body. Once these position and orientations are computed, the collision checking between these rigid bodies can be performed. Performing these collision checks involves ignoring acceptable collisions, such as those between adjacent links of a robot, which are in contact.

In general, the minimum possible distance between two items may be calculated in the following manner, for example, using modeling techniques described in Knoll, that enable modeling of equipment location and distances between various pieces of equipment used in a treatment room.

With the Cartesian position and orientation of moving objects in the treatment room computed using the method described above and for static objects determined from a data file, the minimum possible distance between any two objects is computed as described herein below.

At any time, the modeled location of the various pieces of equipment in the treatment room 100 may be determined. Let S represent the set of all items in the room, D(i,j) represent the modeled Cartesian distance between items (i,j) from S, and $U_i$ and $U_j$ represent the uncertainty in their Cartesian locations. Then the minimum possible distance between any pair of items i and j in S can be used to calculate the safety index $D_{min}(i,j)$ as:

$$D_{min}(i,j)=D(i,j)-U_i-U_j \quad (1)$$

In a preferred embodiment, modeling the minimum distances of items uses the following inputs:
- Couch Roll/Pitch/Yaw
- Couch X/Y/Z position
- Patient 3D external geometry
- Patient location with respect to couch
- Gantry angle
- Snout selection
- Snout extension
- Compensator thickness
- 3D equipment models
- Room 3D models
- (Alternative embodiments may include additional inputs related to radiotherapy treatment delivery)

D(i,j) represents the computed minimum Cartesian distance between two objects i, j. $U_i$ and $U_j$ represent a certain Cartesian buffer around the objects i and j respectively that represents the uncertainty in their position due to various errors as defined below:

The uncertainty Ui is the sum of all Cartesian errors in the location of item i. Ui is further computed from an aggregation of the following sources of Cartesian errors:

$U_{3d}$: For a given rigid body, $U_{3d}$=maximum Cartesian difference between the model of the rigid body and the actual shape of the rigid body as used in the treatment room.

$U_{sensor}$: Mapping of a sensor input to the Cartesian position of a rigid body depends on the type of sensing involved.

For example, if a stereoscopic camera is being used to track the motion of a rigid body, then $U_{sensor}$ will be equal to the Cartesian tracking error of the camera system. In the case of the Proton Nozzle, its Cartesian position is defined by a transformation matrix that is further defined based on the gantry angle. Any errors in measurement of the angle of the beam delivery system 107 may cause an error in the transformation matrix associated with position of the nozzle. $U_{sensor}$ in this case is the maximum Cartesian distance between the position of the nozzle computed using the sensed gantry angle and the position of the nozzle computed using the sensed gantry angle±the sensor error. The same methodology is applied to the computation of $U_{sensor}$ for each link of the robot.

$U_{registration}$: Max Cartesian uncertainty in position of the patient registered relative to the couch.

$U_{stop}$: Max Cartesian uncertainty caused by stopping distances. $U_{stop}$ is the distance required by a moving piece of equipment to come to a complete stop in case of emergency. This uncertainty may be a constant value, or be calculated depending upon the equipment speed.

$U_{comm}$: Max Cartesian uncertainty caused by communications latency. The latency of sensor data is measured as time and is used to compute a sensor error based on the speed of motion of the specific object. This sensor error is then converted to a Cartesian error as represented by $U_{comm}$ in a manner similar to $U_{sensor}$ as described above.

Thus, the modeled distance between any pair of items (i,j) first involves determining the uncorrected locations of two pieces of equipment i and j. This modeled distance is then error corrected by the maximum Cartesian uncertainty in their respective positions (Ui and Uj) and geometry to determine the minimum distance.

Based on the above parameters, for each step in the schedule, the safety index is computed for according to the flow-chart of FIG. 9. First, the distance between the patient 101 and each piece of equipment in the treatment room 100 is computed, step 901, from the following formula:

$$D_{min}(\text{patient}, j) = D(\text{patient}, j) - U_{patient} - U_j$$
$$= D(\text{patient}, j) -$$
$$(U_{3D(patient)} + U_{registration} + U_{stop(i)}) -$$
$$(U_{3D(j)} + U_{sensor} + U_{stop(j)})$$

where j is an index for the various pieces of equipment which includes, for example, the 3D imaging system 201, and the external beam radiation delivery system 107.

Furthermore, minimum distances are calculated for all other pairs of items using the equation (1), step 903.

Having computed minimum distances for each step, these may be used to determine the safety indexes according to the following, step 905:

1. If ($D_{min}$(patient, compensator)≠airgap from treatment plan)
   safetyIndex=0;
2. If ($D_{min}$(patient, snout)<0)
   safetyIndex=0;
3. for all items j where j≠{patient, couch}
   If $D_{min}$(patient, j)<0 then
      safetyIndex=0;
4. for all items i,j where i≠j
   If $D_{min}$(i, j)<0 then
      safetyIndex=0;

Thus, the safety index is set to 0 if the distance between the compensator and the patient 101 is less than an airgap (Airgap) specified in the treatment plan, if the snout is projected to touch the patient 101, if the patient 101 is in contact with any other equipment (other than the couch), or if there is a collision between any of the pieces of equipment.

5.2.2 Dynamic Safety Index

The safety index is also computed based on moving pieces of equipment and the patient 101 and other pieces of equipment, which is illustrated in the flow-chart of FIG. 10. The dynamic step safety index is computed using the following additional parameters:

Maximum allowable couch speed
Maximum allowable robot arm speeds
Maximum allowable couch tilt
Maximum patient momentum/kinetic energy The calculation of the minimum possible distances to the patient and other equipment as described above, i.e., the steps 901, 903, and 905 are computed for each time increment during the execution of a dynamic step.

Multiple subsystems may move simultaneously during beam reconfiguration. During the Safety Index Assignment phase 607, collision free paths for simultaneously moving subsystems are planned according to the following method. Furthermore, during this stage, the durations of each move are computed and stored for later use during time index assignment 606 (see below).

Between each beam in the beam sequence, the direct straight-line path and duration between the start and end point for each piece of moving equipment is computed. The path includes x, y, z position and orientation, and the time of each move.

The path and time to complete steps involving movement of equipment are calculated from models describing the movement of the equipment. The equipment models are mathematical models that include equipment acceleration, maximum speed, and position limits from which motion trajectories may be computed. From the acceleration, maximum speed, and motion trajectories expected time required to execute a workflow step may be calculated by one of the standard methods as described in "Introduction to Robotics: Mechanics and Control" by John J. Craig. For equipment models, trajectory parameters are stored, including acceleration and maximum velocity. Both acceleration and maximum velocity may be user-supplied constraints and generally come from the equipment specification for each piece of equipment, e.g., the patient positioning system 105 may not accelerate to a velocity higher than a specified maximum.

At each time instant over the duration of the moves, all pieces of equipment are checked for collisions as part of the safety index calculation. To be more precise the risk of collision is assessed. If no collisions are detected (or more accurately, if the risk of collision is detected to be high), step 907, the computed duration to be used in the time index assignment is stored, step 909. If a collision is detected, the collision is resolved by sequencing the movements as described below, step 911.

For each pair of colliding subsystems, the start of motion is deferred for one subsystem in the pair until the other subsystem has completed its motion. Furthermore, the duration of the deferred subsystem is adjusted to be the sum of the durations of the pair.

The choice of which subsystem to defer is determined according to user defined priority among all moving subsystems. For example, if priorities are defined as {Couch=0, X-ray=1, Gantry=2, Snout Position=3}, in the event of a collision, all subsystem moves defer to Couch moves, but only Gantry and Snout Position defer to X-ray moves.

For example, timing is adjusted as follows. If the motion of the couch is computed be 3 seconds and the motion of the gantry is computed to be 10 seconds, and both subsystems can be moved simultaneously without collisions, the duration of each would be stored as 3 seconds and 10 seconds, respectively. However, if a collision were detected, the gantry motion would be deferred until the couch motion is completed, and the duration for each move would be stored as 3 seconds for the couch and 13 seconds for the gantry.

The following additional conditions are used to calculate the safety index (step 157):

If (couch speed>max allowable couch speed)
   Safety index=0;
If (equipment (i) speed>max allowed equipment (i) speed)
   Safety index=0;
If(couch tilt>max allowed couch tilt)
   Safety index=0;
If(patient momentum or kinetic energy>max allowed patient momentum or kinetic energy)
   Safety index=0;

In other words, a determination is made whether the couch speed exceeds a determined threshold, whether any piece of equipment i has a speed in excess of the maximum allowed speed for that piece of equipment, e.g., the movement of a robot arm, whether the couch tilt exceeds a maximum allowed tilt, or whether the momentum or kinetic energy of the patient 101 exceeds a permissible threshold. If any of those conditions occur, the safety index is set to zero, i.e., indicating that the safety requirements have been violated.

The above calculations produce an augmented treatment workflow metamodel 817 having safety index assignments. The augmented metamodel 817 is further used to generate an optimal treatment schedule 511 as described below. The computed times 818 for the various moves are used in the time index assignment step 606 (below)

5.3 Time Index Assignment

Returning now to FIG. 8, the process 801 for determining a treatment schedule 511 further includes a step for providing time index assignments, step 606, in which the duration for individual steps in a workflow is assigned based on data in the augmented metamodel 817 or computed times 818 for metamodel steps.

Activities for which the required time is estimated from observation, and stored in a database 803 having observed times, include:
  Patient Setup
  Patient Registration
  Compensator Changes
  Activities by a Radiotherapy Technician Activities for which the required time is estimated from model-based calculations, computed as part of the safety index assignment step 607, and stored in the datastructure 818 having computed times for certain metamodel 817 steps, include:
  Movement of the Patient Positioning System 105 moves (from stored acceleration and maximum speed)
  Changes To Snout Extension (from stored acceleration and maximum speed)
  Nozzle Gantry Motion (from stored acceleration and maximum speed)
  Changes in Nozzle Angle (from stored acceleration and maximum speed)
  Beam Delivery Time (from the treatment plan)

Time index assignments, thus, are made by traversing the augmented metamodel 817. For each step in the metamodel 817, the metamodel step is assigned a time duration either from the database 803 having observed time measures or from the computed times data structure 818. Thus, the output from the time index assignment step 606 is a metamodel 819 that has been augmented with time index assignments per equipment usage according to the resequenced treatment plan.

5.4 Scheduling and Optimization 605

Finally, the process 801 for providing a treatment schedule 511 includes step for providing scheduling and optimization, step 605.

The sections above describe the method by which time and safety indexes are assigned for each action in a workflow metamodel 509. Given these indexes, the treatment plan scheduling and optimization step 605 generates and optimizes the schedule 511 for delivery of a treatment plan 503.

If the metamodel 509 provided by a user is fully constrained, the treatment schedule is already predetermined and no optimizations can be made. A schedule may be calculated by the Bellman-Ford algorithm. The Bellman-Ford algorithm is a standard graph algorithm that determines a minimum cost path between any pair of nodes in a directed acyclic graph. The metamodel 509 is a directed acyclic graph, where the cost of each node is the negative node duration. The start and end times for each action may thus be determined by finding the cost between the start node and every other node. A standard implementation of the Bellman-Ford algorithm is provided through the Boost C++ Libraries community (www*boost*org[2]), though any other implementation is suitable.

[2] Due to the prohibition of functioning hyperlinks in patents, all URLs herein are listed as www*xyz*com wherein each "*" is to be interpreted as a ".".

If the metamodel 509 provided by the user is underconstrained, an automatic scheduling and optimization algorithm is used. Constraint Satisfaction Programming (CSP) techniques are a specific type of logic programming language designed for optimization. ILOG (www*ilog*com) software is an example of a CSP programming language which will generate a schedule. The CSP algorithm attempts to assign start and end times to each task while satisfying all constraints in the metamodel and minimizing the overall execution time.

As an alternative, the metamodel 723 may be translated into another form amenable to solution by an automatic scheduling software. List scheduling is a standardized algorithm which uses precedence relations, durations, and a user supplied heuristic to determine a schedule. An example of existing scheduling software which provides list scheduling and other scheduling algorithms is Torsche from Dept. of Control Engineering, Czech Technical University (http://rtime*felk*cvut*cz/scheduling-toolbox/).

6.0 Treatment Plan Scheduling And Optimization System

Figure 11:
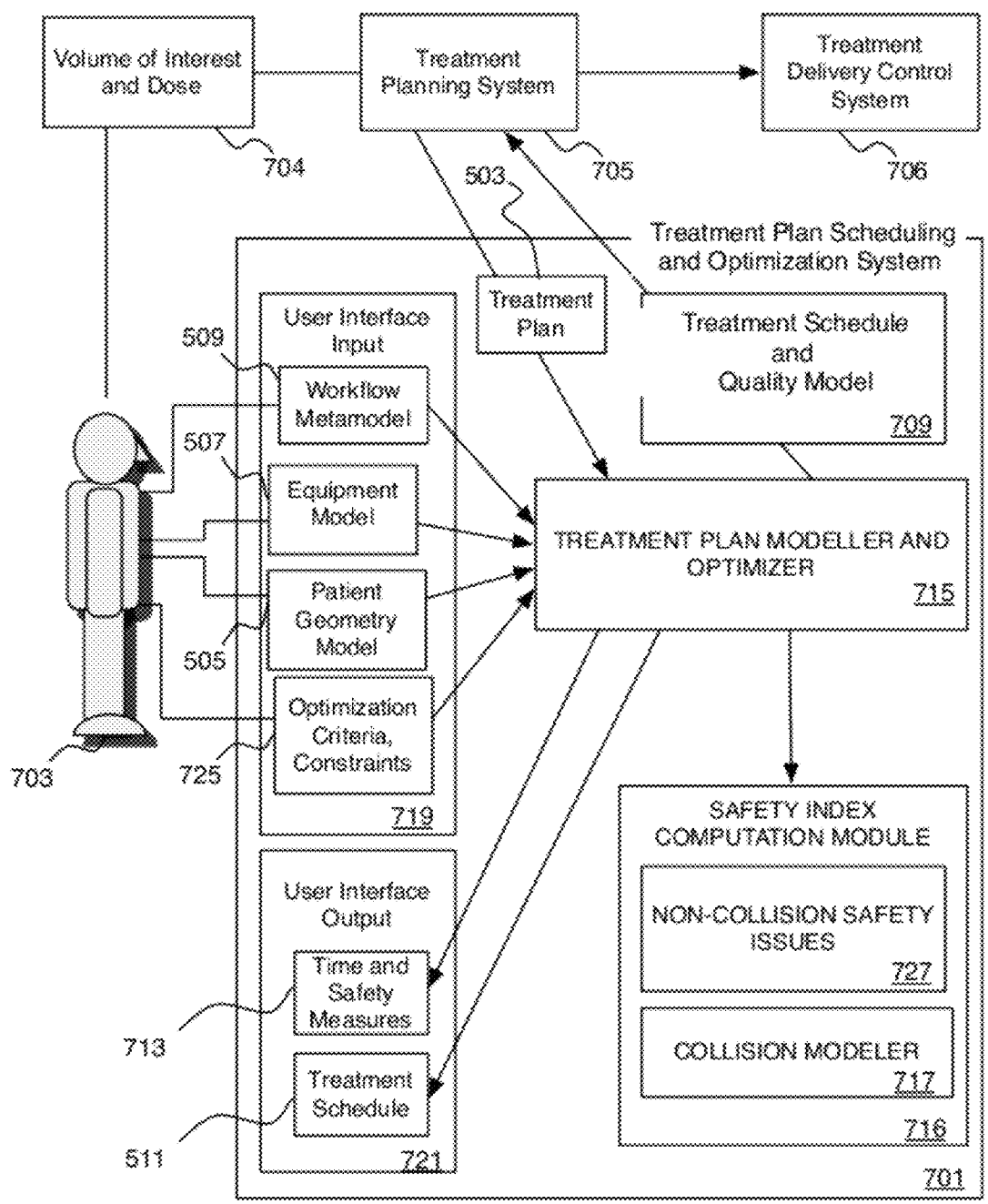
FIG. 11 is a block diagram illustrating the components of an embodiment of a treatment plan scheduling and optimization system.

FIG. 11 is a block diagram illustrating the components of an embodiment of a treatment plan scheduling and optimization system 701 which may operate according to the process 801 illustrated in FIG. 8, which further may correspond to, for example, step 501 in FIG. 5.

The treatment plan scheduling and optimization system 701 may be used in conjunction with delivery of a radiotherapy treatment in multiple ways, e.g., to provide an instance of the treatment schedule 511 fed back to the treatment planning system 705, to provide an optimized schedule 511 to a dosimetrist, physician, or radiotherapist, or to provide time and safety measures 713 on a workflow provided by a user 703. The treatment planning system 705 uses the optimized schedule 511 as an input to the treatment delivery control system 706 to control the patient positioning system 105, the 3D imaging system 201 and the external beam radiation delivery system 107 as discussed above, for example, in conjunction with FIG. 3.

6.1 Treatment Planning Scheduling And Optimization System 701: Modules

On a high-level, in one embodiment, the treatment plan scheduling and optimization stage 501 contains a treatment plan scheduler and optimizer module 715 and a collision modeler 717. Broadly speaking, the treatment plan scheduler and optimizer module 715 calls on the safety index computation module 716 to determine whether particular steps, e.g., movement of equipment, would produce safety index violations, e.g., collisions or near-collisions between equipment, or equipment and patient 101 (by calling on collision modeler 717), or other unacceptable conditions such as excessive couch velocity (by calling on a sub-module 727 for computing such non-collision safety issues. The treatment plan scheduler and optimization system 701 further contains user interfaces 719 and 721, respectively, allowing a user 703, e.g., a dosimetrist, physician or radiotherapy therapist, to enter workflow metamodels 509 used in delivering treatments, optimization criteria and constraints, and for the user 703 to receive results from the treatment plan scheduling and optimization system 701.

6.2 Treatment Planning Scheduling And Optimization Stage 501: Inputs

A user 703, e.g., a dosimetrist or radiotherapy physician, inputs a volume of interest specification and required radiation dosages 704 to the treatment planning system 705. The treatment planning system 705 uses this input to create a treatment plan 503. The treatment plan system 705 may be a treatment planning system such as CMS XiO from CMS, inc., of Maryland Heights, Mo. The treatment plan 503 preferably would be in the DICOM RT Plan and RT Structure Set formats. DICOM (Digital Imaging and Communications in Medicine) is a standard for storing and transmitting information in digital imaging. RT Plan and RT Structure Set are extensions to DICOM for planning and delivering radiotherapy treatments. The RT Plan format provides geometric and dosimetric data for a course of external beam treatment. As such it provides beam angles, intensity, configuration, etc. for the beams required to address the specified volume of interest and dose. The RT Structure Set format provides data specifying patient 101 related structures, e.g., volumes of interest and fixed structures that may be used to register the patient 101 during patient positioning.

The treatment plan 503 is transmitted to the treatment plan scheduling and optimization system 701, in particularly to the treatment plan scheduler and optimizer 715.

Other inputs to the treatment plan scheduling and optimization system 701 include a workflow metamodel 509, equipment models 507 (or equipment specifications from which equipment models may be constructed), and the patient external geometry model 505.

The treatment plan scheduling and optimization system 701 also accepts input parameters such as optimization criteria and safety constraints 725. The optimization criteria include minimization of overall treatment time and maximization of safety index. The safety constraints 725 include parameters such as whether to allow simultaneous movement of robotic equipment, e.g., the imaging equipment 201 and the patient positioning system 105. Safety constraints 725 may also specify minimum distances allowed between various pieces of equipment, and between these pieces of equipment and the patient 101.

6.3 Treatment Plan Scheduling And Optimization System 701: Outputs

A first output to the treatment plan scheduling and optimization system 701 is a schedule and quality model 709 of a workflow for a submitted treatment plan 707. The schedule and quality model 709 includes start and end time assignments for each step in the workflow for delivering the treatment plan 707, a safety index for each step in the workflow, and an aggregate time and safety index for the entire workflow, each computed, for example, as described hereinabove in conjunction with FIGS. 5 through 10.

The schedule and quality model 709 may be either provided as feedback to the treatment planning system 705 or as time and safety measures 713 to the user 703 via the user output interface 721.

6.4 Treatment Plan Modeling And Optimization System 701: Calculations

According to an embodiment, a method 801 (described above in conjunction with FIG. 8) provides workflow modeling and optimization in which the following steps are performed:

Receive a treatment plan 503 from a treatment planning stage 403
Receive a metamodel 509 for a treatment plan 503
Model the equipment involved in delivery of the treatment plan 507
Receive Patient 3D External Geometry Data 507
Resequence the beam order according to a user supplied heuristic, step 608
Determine safety indices for the various steps of the workflow that includes collision modeling and consideration of other safety factors, step 607
Determine a safety index for the entire workflow, step 607
Determine durations for the various steps of the workflow, step 606
Determine a schedule for the entire workflow, step 605
Provide alternative schedules with improved time indexes while not violating safety factors, i.e., without exceeding a minimum safety index, step 605

The process 801 for providing the above mentioned steps may be performed by a treatment plan modeler and optimizer module 715 operable to implement aforementioned process 801 steps.

For example, the treatment plan scheduler and optimization module 715 also determines a safety index for each step in the delivery of a treatment plan according to the method step 607 for assigning safety index. In the computation of safety indexes, the treatment plan scheduler and optimizer module 715 may call upon a collision modeler module 717, which may be an implementation of the equipment modeling and collision modeling techniques set forth in Knoll, to perform equipment modeling and collision modeling. As noted above, such a module may accept as input the locations and orientations of each object in the treatment room, including the patient 101, a scene configuration file which provides the relationship between objects in the room, and object geometries for each object in the treatment room. The object models include patient surface scanning models describing the geometric shape of the patient 101.

The collision modeler module 717 may build upon software programs such as SOLID which is provided under the GNU General Public License by the Department of Mathematics and Computing Science, Eindhoven University of Technology, P.O. Box 513, 5600 MB Eindhoven, The Netherlands.

The treatment plan scheduler and optimizer 715 determines the duration for certain individual steps in a workflow metamodel 509 based on data in the metamodel 509 or data stored in a database and assigns time indexes to the individual steps of metamodel 509 using, for example, the methods described herein above in conjunction with step 606 of FIG. 8.

The treatment plan scheduler and optimizer 715 also provides treatment schedules 511 with a reordering of beam sequences, for example, as described in conjunction with step 608 of FIG. 8.

The sections above describe the method by which the treatment plan scheduler and optimizer determine time and safety indexes for each action of a treatment schedule 511. Given these indexes, the treatment plan scheduler and optimizer 715 generates and optimizes the schedule 511 for delivery of a treatment plan 503, for example, using the method described hereinabove in conjunction with the scheduling and optimization step 605 of FIG. 8.

7.0 Hardware

Figure 12:
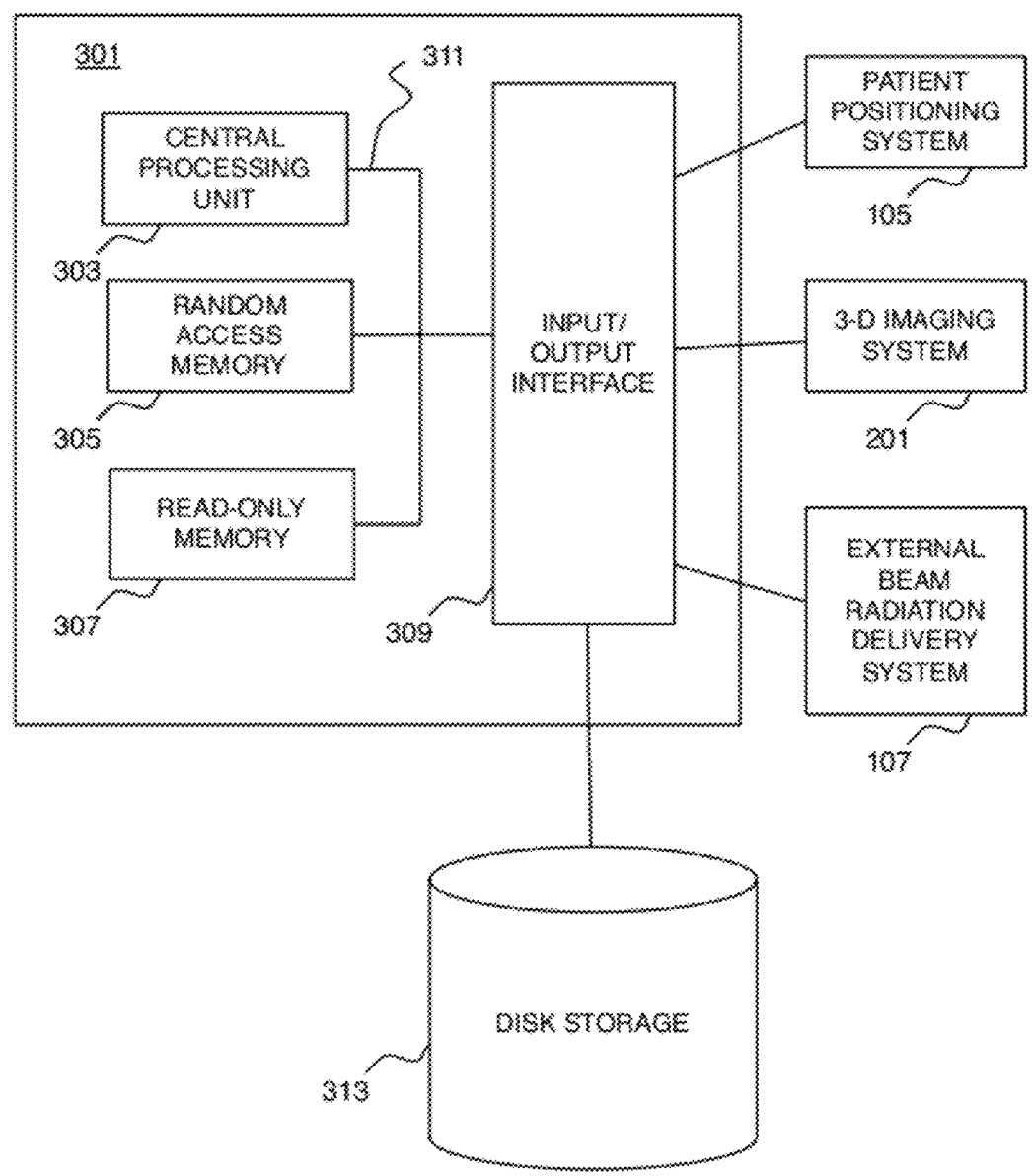
FIG. 12 is a schematic illustration of one example of the hardware aspect a radio-therapy control system.

FIG. 12 is a schematic illustration of one example of the hardware aspect of a radio-therapy control system 301. The control system 301 includes a central processing unit 303, a random access memory 305, a read-only memory 307, and an input/output interface 309, all connected via a bus 311. A disk storage device 313 is connected to the input/output interface 309. The central processing units operations are controlled by instructions found in computer programs stored in the disk storage device 313 and in the read-only memory 307.

Thus, the program instructions that make up the treatment plan scheduling and optimization system 701 may be stored in the disk storage device 313. When executed by the central processing unit 303, these instructions are loaded into the read access memory 305 and cause the central processing unit to execute certain operations, e.g., deliver instructions to the treatment delivery equipment 107, the patient positioning system 105, or the 3D imaging system 201.

From the foregoing it will be apparent that a system and method has been described herein that provides for improved modeling of the workflow associated with the delivery of radiotherapy treatment plans. Such improved modeling assures that safety requirements are met while optimizing the schedule for time. The modeled treatment plan provides an improvement that allows for more efficient utilization of radiotherapy treatment rooms thereby reducing costs and improving the experience of patients.

While embodiments of the present radiation therapy schedule optimization system is described herein, for purposes of example, relative to proton therapy, the techniques described herein are equally applicable to other forms of external beam radiotherapy as well as other medical treatment delivery systems that involve the movement of patients, and reconfiguration and movement of equipment according to a schedule specifying the actions of the actors involved (actors including therapists and pieces of equipment).

A particular architecture for a workflow scheduling and optimization system has been described hereinabove for exemplary purposes. Alternative arrangements may be employed to execute the methods described. Such alternatives must be deemed included in the scope of the claims.

Although specific embodiments of the invention have been described and illustrated, the invention is not to be limited to the specific forms or arrangements of parts so described and illustrated. The invention is limited only by the claims.

We claim:

1. A method for operating radio-therapy equipment comprising a radio-therapy control system, having a central processing system and memory, to control radiotherapy treatment room equipment, including at least one piece of radio-therapy equipment selected from patient positioning equipment, proton beam delivery equipment, and imaging equipment, providing an external beam radiotherapy treatment at a treatment center, comprising:

receiving a workflow metamodel into the radio-therapy control system, the workflow metamodel specifying steps carried out at the treatment center when delivering treatment wherein the metamodel comprises a set of actions including an action performed by the at least one piece of radio-therapy equipment, execution time required for each action, actors required for each action, and restrictions on ordering of actions;

receiving into the radio-therapy control system a treatment plan describing steps executed by at least one piece of radio-therapy equipment;

operating the radio-therapy control system to determine a treatment schedule defining a sequence and timing of activities corresponding to the workflow metamodel and the treatment plan that avoids violating a safety threshold of a safety index associated with executing the treatment schedule, the determining of a treatment schedule comprising determining alternative treatment schedules that are possible according to the workflow metamodel;

computing a safety index for each such alternative treatment schedule using a function having a parameter selected from constraints on couch angles, couch speeds, patient proximity to individual pieces of equipment, couch proximity to individual pieces of equipment, speed of the couch positioner mechanism, and the range of motion of the couch positioner mechanism; and selecting one alternative treatment schedule having a safety index satisfying the safety threshold and that provides a schedule optimized to minimize treatment time, or to maximize patient or equipment safety; and operating the at least one piece of radio-therapy equipment according to the alternative treatment schedule.

2. The method of operating a radio-therapy equipment for providing an external beam radiotherapy treatment of claim 1, wherein the safety index is computed by using a model of the at least one piece of radio-therapy equipment, a model of a patient to determine the risk of collisions between the at least one piece of radio-therapy equipment and the patient.

3. The method of operating a radio-therapy equipment for providing an external beam radiotherapy treatment of claim 1 wherein the at least one piece of radio-therapy equipment comprises a first piece of radio-therapy equipment and a second piece of equipment and wherein computing the safety index further comprises using a model of the first piece of radio-therapy equipment and a model of a second piece of equipment.

4. The method of operating a radio-therapy equipment providing an external beam radiotherapy treatment of claim 1 wherein operating the radio-therapy control system to determine the safety index comprises operating the radio-therapy control system to simulate motion of at least one piece of radio-therapy equipment and to determine, for a plurality of time increments, distances between at least one piece of equipment and the patient.

5. The method of operating a radio-therapy equipment for providing an external beam radiotherapy treatment of claim 1 wherein operating the radio-therapy control system to determine the safety index comprises operating the radio-therapy control system to take into account estimated errors in the model of the at least one piece of radio-therapy equipment and a model of a patient.

6. The method of operating a radio-therapy equipment for providing an external beam radiotherapy treatment of claim 5 wherein to take into account the estimated errors in the model of the at least one piece of radio-therapy equipment and a model of a patient comprises to take into account at least one uncertainty selected from the set including the maximum Cartesian difference between the model of the rigid body of a piece of equipment or the patient and the actual shape of the rigid body of a piece of equipment or the patient, the uncertainty associated with a sensor tracking motion of a rigid body of a piece of equipment, the uncertainty of the position of the registered position of the patient and the actual position of the patient, uncertainty associated with stopping distance of a piece of equipment, uncertainty caused by communications latency.

7. The method of operating a radio-therapy equipment for providing an external beam radiotherapy treatment of claim 1 wherein the workflow metamodel is described as a sequence of steps each having associated therewith an action, a set of resources and actors, constraints between actions, and an expected elapsed time for executing the action, and wherein the determination of alternative treatment schedules and selection of one alternative treatment schedule associated with delivery of the treatment plan comprises resequencing the actions in the workflow metamodel, or identifying sequences of sub-steps that may be performed in parallel thereby reducing a cumulative elapsed time, or any combination of these steps.

8. The method of operating a radio-therapy equipment for providing an external beam radiotherapy treatment of claim 7 wherein operating the radio-therapy control system to compute the safety index comprises using a model of the at least one piece of radio-therapy equipment, a model of a patient to determine the risk of collisions between the at least one piece of radio-therapy equipment and the patient; and further comprising:
based on a determination that a risk of collision is high, operating the radio-therapy control system to determine a sequence of movement of pieces of equipment according to a list of priorities that prioritizes the order in which different pieces of equipment are to be moved when a risk of collision is high.

9. The method of operating a radio-therapy equipment for providing an external beam radiotherapy treatment of claim 7 wherein the expected elapsed time is computed from a model of an actor performing the action wherein the actor is selected from the at least one piece of radiotherapy equipment and a radio therapy technician.

10. The method of operating a radio-therapy equipment for providing an external beam radiotherapy treatment of claim 1 further comprises excluding a candidate treatment schedule from consideration if the optimization results in a safety index violating a proscribed constraint.

11. The method of operating a radio-therapy equipment for providing an external beam radiotherapy treatment of claim 1 further comprising operating the radio-therapy control system to identify tasks that may be performed in parallel by a plurality of resources and scheduling the tasks that may be performed in parallel wherein a first resource performs a first task that may be performed in parallel with a second task and a second resource performs the second task that may be performed in parallel with the first task whereby the first and second tasks that may be performed in parallel are performed in parallel.

12. The method of operating a radio-therapy equipment for providing an external beam radiotherapy treatment of claim 1 wherein the determination of the optimized schedule is performed by a constraint programming.

13. The method of operating a radio-therapy equipment for providing an external beam radiotherapy treatment of claim 1 wherein the determination of the optimized schedule is performed using the Bellman-Ford algorithm.

14. The method of operating a radio-therapy equipment for providing an external beam radiotherapy treatment of claim 1 further comprising:
operating the radio-therapy control system to resequence beams specified in the treatment plan by sorting beam reconfiguration operations according to a precedence relationship between the various types of configuration changes required going from one beam configuration to a next beam configuration encountered in the treatment plan.

15. The method of operating a radio-therapy equipment for providing an external beam radiotherapy treatment of claim 14 wherein each beam is defined by a plurality of items selected from snout selection, compensator thickness, beam delivery angle, patient support angle, isocenter, snout extension and the sorting is performed by a lexicographical sorting on the selected items.

16. The method of operating a radio-therapy equipment for providing an external beam radiotherapy treatment of claim 1, wherein the safety index is computed as a function of constraints on couch angles.

17. The method of operating a radio-therapy equipment for providing an external beam radiotherapy treatment of claim 1, wherein the safety index is computed as a function of constraints on couch speeds.

18. The method of operating a radio-therapy equipment for providing an external beam radiotherapy treatment of claim 1, wherein the safety index is computed as a function of constraints on patient proximity to individual pieces of equipment.

19. The method of operating a radio-therapy equipment for providing an external beam radiotherapy treatment of claim 1, wherein the safety index is computed as a function of constraints on speed of the couch positioner mechanism.

20. The method of operating a radio-therapy equipment for providing an external beam radiotherapy treatment of claim 1, wherein the safety index is computed as a function of constraints on the range of motion of the couch positioner mechanism.

21. A radio-therapy control computer having a central processing unit and a memory containing computer program instructions, the central processing unit operable to execute the computer program instructions, and wherein the radio-therapy control computer is connected to at least one piece of external beam radiotherapy delivery equipment, the instructions including instruction to cause the computer to direct the at least one piece of external beam radio-therapy system to perform a sequence of actions in the provisioning of an external beam radiotherapy treatment, the instructions comprising instructions to cause the central processing unit to:
receive a workflow metamodel specifying steps carried out at the treatment center when delivering treatment wherein the metamodel comprises a set of actions including an action performed by the at least one piece of radio-therapy equipment, execution time required for each action, actors required for each action, and restrictions on ordering of actions;
receive a treatment plan describing steps executed by at least one piece of radio-therapy equipment;
determine a treatment schedule defining a sequence and timing of activities corresponding to the workflow metamodel and the treatment plan that avoids violating a safety threshold of a safety index associated with executing the treatment schedule, the determining of a treatment schedule comprising instructions to determine alternative treatment schedules that are possible according to the workflow metamodel;

compute a safety index for each alternative treatment schedule using a function having a parameter selected from constraints on couch angles, couch speeds, patient proximity to individual pieces of equipment, couch proximity to individual pieces of equipment, speed of the couch positioner mechanism, and the range of motion of the couch positioner mechanism; and select one alternative treatment schedule having a safety index satisfying the safety threshold and that provides a schedule optimized to minimize treatment time or to maximize patient or equipment safety; and control the operation of the at least one piece of radio-therapy equipment according to the alternative treatment schedule.

22. The radio-therapy control computer of claim 21, wherein the safety index is computed by using a model of the at least one piece of radio-therapy equipment, a model of a patient to determine the risk of collisions between the at least one piece of radio-therapy equipment and the patient.

23. The radio-therapy control computer of claim 21 wherein the at least one piece of radio-therapy equipment comprises a first piece of radio-therapy equipment and a second piece of equipment and wherein computing the safety index further comprises using a model of the first piece of radio-therapy equipment and a model of a second piece of equipment.

24. The radio-therapy control computer of claim 21 wherein the instructions to compute the safety index comprise instructions to simulate motion of the at least one piece of radio-therapy equipment and to computer, for a plurality of time increments, distances between the at least one piece of equipment and the patient.

25. The radio-therapy control computer of claim 21 wherein the instructions to compute the safety index comprise instructions to take into account estimated errors in the model of the at least one piece of radio-therapy equipment and a model of a patient.

26. The radio-therapy control computer of claim 25 wherein the instructions to take into account the estimated errors in the model of the at least one piece of radio-therapy equipment and a model of a patient comprises instructions to take into account at least one uncertainty selected from the set including the maximum Cartesian difference between the model of the rigid body of a piece of equipment or the patient and the actual shape of the rigid body of a piece of equipment or the patient, the uncertainty associated with a sensor tracking motion of a rigid body of a piece of equipment, the uncertainty of the position of the registered position of the patient and the actual position of the patient, uncertainty associated with stopping distance of a piece of equipment, uncertainty caused by communications latency.

27. The radio-therapy control computer of claim 21 wherein the workflow metamodel is described as a sequence of steps each having associated therewith an action, a set of resources and actors, constraints between actions, and an expected elapsed time for executing the action, and wherein the determination of alternative treatment schedules and selection of one alternative treatment schedule associated with delivery of the treatment plan comprises resequencing the actions in the workflow metamodel, or identifying sequences of sub-steps that may be performed in parallel thereby reducing a cumulative elapsed time, or any combination of these steps.

28. The radio-therapy control computer of claim 27 wherein computing the safety index comprises using a model of the at least one piece of radio-therapy equipment, a model of a patient to determine the risk of collisions between the at least one piece of radio-therapy equipment and the patient; and further comprising instructions to:

based on a determination that if a risk of collision is high, sequence movement of pieces of equipment according to a list of priorities that prioritizes the order in which different pieces of equipment are to be moved when a risk of collision is high.

29. The radio-therapy control computer of claim 27 wherein the instructions to cause the computer system to compute the expected elapsed time includes instructions to compute the expected elapsed time from a model of an actor performing the action wherein the actor is selected from the at least one piece of radiotherapy equipment and a radio therapy technician.

30. The radio-therapy control computer of claim 21 further comprises instructions to cause the computer system to exclude a schedule optimization from consideration if the optimization results in a safety index violating a proscribed constraint.

31. The radio-therapy control computer of claim 21 further comprising instructions to cause the computer system to identify tasks that may be performed in parallel by a plurality of resources and to schedule the tasks that may be performed in parallel wherein a first resource performs a first task that may be performed in parallel with a second task and a second resource performs the second task that may be performed in parallel with the first task whereby the first and second tasks that may be performed in parallel are performed in parallel.

32. The radio-therapy control computer of claim 21 wherein the instructions to determine the optimized schedule include instructions to cause the computer system to determine the optimized schedule by constraint programming.

33. The radio-therapy control computer of claim 21 wherein the instructions to determine the optimized schedule include instructions to cause the computer system to determine the optimized schedule by applying the Bellman-Ford algorithm.

34. The radio-therapy control computer of claim 21 further comprising instructions:

to resequence beams specified in the treatment plan by sorting beam reconfiguration operations according to a precedence relationship between the various types of configuration changes required going from one beam configuration to a next beam configuration encountered in the treatment plan.

35. The radio-therapy control computer of claim 34 wherein each beam is defined by a plurality of items selected from snout selection, compensator thickness, beam delivery angle, patient support angle, isocenter, snout extension and the sorting is performed by a lexicographical sorting on the selected items.

36. The radio-therapy control computer of claim 21, wherein the safety index is computed as a function of constraints on couch angles.

37. The radio-therapy control computer of claim 21, wherein the safety index is computed as a function of constraints on couch speeds.

38. The radio-therapy control computer of claim 21, wherein the safety index is computed as a function of constraints on patient proximity to individual pieces of equipment.

39. The radio-therapy control computer of claim 21, wherein the safety index is computed as a function of constraints on speed of the couch positioner mechanism.

40. The radio-therapy control computer of claim 21, wherein the safety index is computed as a function of constraints on the range of motion of the couch positioner mechanism.

41. A non-transitory computer readable storage medium for storing computer program instructions, the computer readable storage medium comprising:
- instructions to cause a computer system, connected to an external beam radiotherapy treatment system at a treatment center, to:
  - determine a workflow metamodel specifying steps carried out at the treatment center when delivering treatment wherein the metamodel comprises a set of actions, execution time required for each action, actors required for each action, and restrictions on ordering of actions;
  - receive a treatment plan describing steps executed by at least one piece of radio-therapy equipment; and
  - determine a treatment schedule defining a sequence and timing of activities corresponding to the workflow metamodel and the treatment plan that avoids violating a safety threshold of a safety index associated with executing the treatment schedule, the instructions to cause the computer system to determine a treatment schedule comprises instructions to cause the computer system to
  - determine alternative treatment schedules that are possible according to the workflow metamodel;
  - compute a safety index for each alternative treatment schedule using a function having a parameter selected from constraints on couch angles, couch speeds, patient proximity to individual pieces of equipment, couch proximity to individual pieces of equipment, speed of the couch positioner mechanism, and the range of motion of the couch positioner mechanism; and
  - select one alternative treatment schedule having a safety index satisfying the safety threshold and that provides a schedule optimized to minimize treatment time or to maximize patient or equipment safety.

42. The non-transitory computer readable storage medium for storing computer program instructions of claim 41 wherein the instructions to compute the safety index include instruction to cause the computer system to compute the safety index by using a model of the at least one piece of radio-therapy equipment, a model of a patient to determine the risk of collisions between the at least one piece of radio-therapy equipment and the patient.

43. The non-transitory computer readable storage medium for storing computer program instructions of claim 41 wherein the at least one piece of radio-therapy equipment comprises a first piece of radio-therapy equipment and a second piece of equipment and wherein computing the safety index further comprises using a model of the first piece of radio-therapy equipment and a model of a second piece of equipment.

44. The non-transitory computer readable storage medium for storing computer program instructions of claim 41 wherein the instructions to compute the safety index include instruction to cause the computer system to simulate motion of at least one piece of radio-therapy equipment and to determine, for a plurality of time increments, distances between at least one piece of equipment and the patient.

45. The non-transitory computer readable storage medium for storing computer program instructions of claim 41 wherein the instructions to compute the safety index include instruction to cause the computer system to determine the safety index taking into account estimated errors in the model of the at least one piece of radio-therapy equipment and a model of a patient.

46. The non-transitory computer readable storage medium for storing computer program instructions of claim 45 wherein the instructions computing the estimated errors in the model of the at least one piece of radio-therapy equipment and a model of a patient comprises instructions to take into account at least one uncertainty selected from the set including the maximum Cartesian difference between the model of the rigid body of a piece of equipment or the patient and the actual shape of the rigid body of a piece of equipment or the patient, the uncertainty associated with a sensor tracking motion of a rigid body of a piece of equipment, the uncertainty of the position of the registered position of the patient and the actual position of the patient, uncertainty associated with stopping distance of a piece of equipment, uncertainty caused by communications latency.

47. The non-transitory computer readable storage medium for storing computer program instructions of claim 41 wherein the workflow metamodel is described as a sequence of steps each having associated therewith an action, a set of resources and actors, constraints between actions, and an expected elapsed time for executing the action, and wherein the determination of the alternative treatment schedules and selection of one alternative treatment schedule associated with executing the treatment plan comprises resequencing the actions in the workflow metamodel, or identifying sequences of sub-steps that may be performed in parallel thereby reducing a cumulative elapsed time, or any combination of these steps.

48. The non-transitory computer readable storage medium for storing computer program instructions of claim 47 wherein computing the safety index is by using a model of the at least one piece of radio-therapy equipment, a model of a patient to determine the risk of collisions between the at least one piece of radio-therapy equipment and the patient; and further comprising instructions to cause a computer system connected to an external beam radiotherapy treatment system to:
- based on a determination that if a risk of collision is high, sequencing movement of pieces of equipment according to a list of priorities that prioritizes the order in which different pieces of equipment are to be moved when a risk of collision is high.

49. The non-transitory computer readable storage medium for storing computer program instructions of claim 47 further comprising instruction to cause a computer system to compute the expected elapsed time from a model of an actor performing the action wherein the actor is selected from the at least one piece of radiotherapy equipment and a radio therapy technician.

50. The non-transitory computer readable storage medium for storing computer program instructions of claim 41 further comprising instructions to cause a computer system connected to an external beam radiotherapy treatment system to exclude a candidate treatment schedule from consideration if the optimization results in a safety index violating a proscribed constraint.

51. The non-transitory computer readable storage medium for storing computer program instructions of claim 41 further comprising instruction to cause a computer system to identify tasks that may be performed in parallel by a plurality of resources and scheduling the tasks that may be performed in parallel wherein a first resource performs a first task that may be performed in parallel with a second task and a second resource performs the second task that may be performed in parallel with the first task whereby the first and second tasks that may be performed in parallel are performed in parallel.

52. The non-transitory computer readable storage medium for storing computer program instructions of claim 41 wherein the instruction to determine the optimized schedule includes instructions to determine the optimized schedule by a constraint programming.

53. The non-transitory computer readable storage medium for storing computer program instructions of claim 41 wherein the instruction to determine the optimized schedule includes instructions to determine the optimized schedule by using the Bellman-Ford algorithm.

54. The non-transitory computer computer readable storage medium for storing computer program instructions of claim 41 further comprising instruction to cause a computer system to:
   resequence beams specified in the treatment plan by sorting beam reconfiguration operations according to a precedence relationship between the various types of configuration changes required going from one beam configuration to a next beam configuration encountered in the treatment plan.

55. The non-transitory computer readable storage medium for storing computer program instructions of claim 54 wherein each beam is defined by a plurality of items selected from snout selection, compensator thickness, beam delivery angle, patient support angle, isocenter, snout extension and the sorting is performed by a lexicographical sorting on the selected items.

56. The non-transitory computer readable storage medium for storing computer program instructions of claim 41, wherein the safety index is computed as a function of constraints on couch angles.

57. The non-transitory computer readable storage medium for storing computer program instructions of claim 41, wherein the safety index is computed as a function of constraints on couch speeds.

58. The non-transitory computer readable storage medium for storing computer program instructions of claim 41, wherein the safety index is computed as a function of constraints on patient proximity to individual pieces of equipment.

59. The non-transitory computer readable storage medium for storing computer program instructions of claim 41, wherein the safety index is computed as a function of constraints on speed of the couch positioner mechanism.

60. The non-transitory computer readable storage medium for storing computer program instructions of claim 41, wherein the safety index is computed as a function of constraints on the range of motion of the couch positioner mechanism.

\* \* \* \* \*